United States Patent
Alim et al.

(10) Patent No.: US 12,071,515 B2
(45) Date of Patent: *Aug. 27, 2024

(54) HIGH DYNAMIC RANGE TWO-STAGE PHOTOPOLYMERS

(71) Applicant: THE REGENTS OF THE UNIVERSITY OF COLORADO, A BODY CORPORATE, Denver, CO (US)

(72) Inventors: Marvin D. Alim, Kirkland, WA (US); Christopher N. Bowman, Boulder, CO (US); Sudheendran Mavila, Boulder, CO (US); Robert R. McLeod, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 291 days.

This patent is subject to a terminal disclaimer.

(21) Appl. No.: 16/972,884

(22) PCT Filed: Jun. 10, 2019

(86) PCT No.: PCT/US2019/036375
§ 371 (c)(1),
(2) Date: Dec. 7, 2020

(87) PCT Pub. No.: WO2019/237117
PCT Pub. Date: Dec. 12, 2019

(65) Prior Publication Data
US 2021/0246266 A1 Aug. 12, 2021

Related U.S. Application Data

(60) Provisional application No. 62/682,659, filed on Jun. 8, 2018.

(51) Int. Cl.
*C08G 75/02* (2016.01)
*C08F 2/50* (2006.01)
(Continued)

(52) U.S. Cl.
CPC ............ *C08G 75/02* (2013.01); *C08F 2/50* (2013.01); *C08F 20/38* (2013.01); *C08F 28/04* (2013.01);
(Continued)

(58) Field of Classification Search
None
See application file for complete search history.

(56) References Cited

U.S. PATENT DOCUMENTS

| 5,225,472 A | 7/1993 | Cameron et al. |
| 5,342,724 A | 8/1994 | Wilson |

(Continued)

FOREIGN PATENT DOCUMENTS

| JP | 2006349770 A | 12/2006 |
| JP | 2017014213 A * | 1/2017 |

(Continued)

OTHER PUBLICATIONS

International Search Report and Written Opinion dated Sep. 9, 2019 for International Application No. PCT/US19/36375.

(Continued)

*Primary Examiner* — Martin J Angebranndt
(74) *Attorney, Agent, or Firm* — Saul Ewing LLP; Kathryn Doyle; Domingos J. Silva

(57) ABSTRACT

The present invention, in one aspect, relates to monomers and photopolymers that exhibit a high refractive index. The photopolymers of the invention have properties suitable for fabricating holographic optical elements (HOEs).

20 Claims, 19 Drawing Sheets

(51) Int. Cl.

| | | |
|---|---|---|
| *C08F 20/38* | (2006.01) | |
| *C08F 28/04* | (2006.01) | |
| *G02B 5/32* | (2006.01) | |
| *G03F 7/004* | (2006.01) | |
| *G03H 1/02* | (2006.01) | |
| *G03F 7/00* | (2006.01) | |

(52) U.S. Cl.
CPC ............. *G02B 5/32* (2013.01); *G03F 7/004* (2013.01); *G03F 7/001* (2013.01); *G03H 1/024* (2013.01); *G03H 2260/12* (2013.01)

(56) References Cited

U.S. PATENT DOCUMENTS

| | | | |
|---|---|---|---|
| 6,040,389 A | 3/2000 | Wideman et al. | |
| 6,780,546 B2 | 8/2004 | Trentler et al. | |
| 6,864,019 B2 | 3/2005 | Hegel et al. | |
| 6,939,648 B2 | 9/2005 | Dhar et al. | |
| 7,671,145 B2 | 3/2010 | Sawant et al. | |
| 7,943,680 B2 | 5/2011 | Bowman et al. | |
| 8,323,854 B2 | 12/2012 | Askham | |
| 8,404,758 B2 | 3/2013 | Bowman et al. | |
| 8,658,332 B2 | 2/2014 | Askham | |
| 9,057,946 B2 | 6/2015 | Facke et al. | |
| 9,410,030 B2 | 8/2016 | Joly et al. | |
| 2003/0224250 A1* | 12/2003 | Setthachayanon | G03F 7/027 430/1 |
| 2005/0049376 A1* | 3/2005 | Chisholm | C08F 246/00 549/72 |
| 2005/0259303 A1 | 11/2005 | Setthachayanon et al. | |
| 2006/0036110 A1 | 2/2006 | Brown et al. | |
| 2006/0194120 A1 | 8/2006 | Cole et al. | |
| 2006/0195120 A1* | 8/2006 | Nobles | A61B 17/0482 606/144 |
| 2007/0078198 A1* | 4/2007 | Otsuji | C08F 22/1006 523/120 |
| 2007/0166625 A1 | 7/2007 | Cole et al. | |
| 2007/0231744 A1 | 10/2007 | Sasao et al. | |
| 2007/0240609 A1 | 10/2007 | Husler et al. | |
| 2007/0297944 A1* | 12/2007 | Wendland | G01J 1/04 257/E27.129 |
| 2008/0145545 A1* | 6/2008 | Chisholm | C09D 133/14 524/789 |
| 2009/0023879 A1* | 1/2009 | Wanders | A61L 27/16 560/221 |
| 2009/0054978 A1* | 2/2009 | Wanders | A61L 27/50 264/1.36 |
| 2010/0039685 A1 | 2/2010 | Miki et al. | |
| 2010/0086860 A1 | 4/2010 | Roelle et al. | |
| 2010/0086861 A1 | 4/2010 | Weiser et al. | |
| 2011/0073171 A1* | 3/2011 | Pickett | C08K 5/3492 136/255 |
| 2011/0236803 A1 | 9/2011 | Weiser et al. | |
| 2012/0214090 A1 | 8/2012 | Weiser et al. | |
| 2012/0214895 A1 | 8/2012 | Roelle et al. | |
| 2012/0231377 A1 | 9/2012 | Weiser et al. | |
| 2012/0295288 A1 | 11/2012 | Yu et al. | |
| 2012/0321998 A1 | 12/2012 | Rölle et al. | |
| 2013/0035414 A1* | 2/2013 | Higgs | C08F 22/10 522/182 |
| 2013/0252140 A1* | 9/2013 | Facke | C09D 175/04 430/2 |
| 2014/0295328 A1 | 10/2014 | Weiser et al. | |
| 2015/0283039 A1 | 10/2015 | Joly et al. | |
| 2016/0229800 A1 | 8/2016 | Fornof et al. | |
| 2018/0217312 A1* | 8/2018 | Hiraoka | C08K 5/378 |
| 2018/0275603 A1 | 9/2018 | Kikuchi et al. | |
| 2020/0157271 A1 | 5/2020 | Hwang et al. | |
| 2021/0155599 A1* | 5/2021 | Purvis | C07C 333/04 |
| 2021/0292482 A1* | 9/2021 | Bowman | C08K 5/37 |
| 2022/0119567 A1* | 4/2022 | Bowman | C08G 18/672 |
| 2022/0153693 A1* | 5/2022 | Purvis, II | C07C 271/16 |
| 2022/0153895 A1* | 5/2022 | Purvis, II | C07F 9/18 |
| 2022/0299867 A1 | 9/2022 | Lane et al. | |
| 2022/0299868 A1 | 9/2022 | Lane et al. | |
| 2022/0299938 A1 | 9/2022 | Lane et al. | |

FOREIGN PATENT DOCUMENTS

| | | |
|---|---|---|
| WO | WO-2017174545 A1 * | 10/2017 |
| WO | 2018039331 A1 | 3/2018 |

OTHER PUBLICATIONS

Alim, et al., "High Dynamic Range (delta n) Two-Stage Photopolymers via Enhanced Solubility of a High Refractive Index Acrylate Writing Monomer", ACS Appl Mater Interfaces, vol. 10, 2018, pp. 1217-1224.

Ayres, et al., "Holographic Data Storage at 2+ Tbit/in 2", Bjelkhagen, H. I., Bove, V. M., Eds.; International Society for Optics and Photonics, vol. 9386, 2015, 93860G.

Bruder, et al., "The Chemistry and Physics of Bayfol® HX Film Holographic Photopolymer", Polymers (Basel), 9(10), 2017, 472.

Peng, et al., "Facile Image Patterning via Sequential Thiol-Michael/ Thiol-Yne Click Reactions", Chem. Mater., 26(23), 2014, 6819 6826.

Yao, et al., "Thiol-yne click polymerization", Chinese Science Bulletin, vol. 58, No. 22, Aug. 2013, pp. 2711-2718.

"International Search Report and Written Opinion dated May 6, 2020 for International Application No. PCT/US2020/018621".

Fildes, et al., "Formation of block copolymers form polyurethanes containing reactive disulfides", J. Poly. Sci., Part A-1, vol. 10, 1972, 151-161.

Haddleton, et al., "Alpha,omega-Dihydroxy telechelic poly(methyl methacrylate) via beta-scission (radical addition fragmentation) chain transfer polymerization by macromonomer chain transfer agents, as prepared by catalytic chain transfer polymerization", Macromol. Chem. Phys., vol. 197, 1996, 3027-3042.

\* cited by examiner

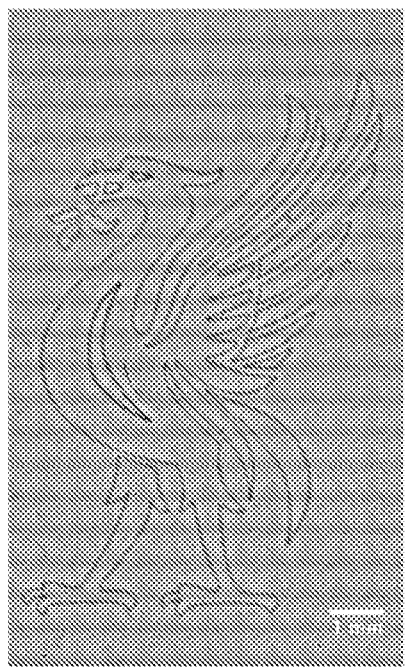
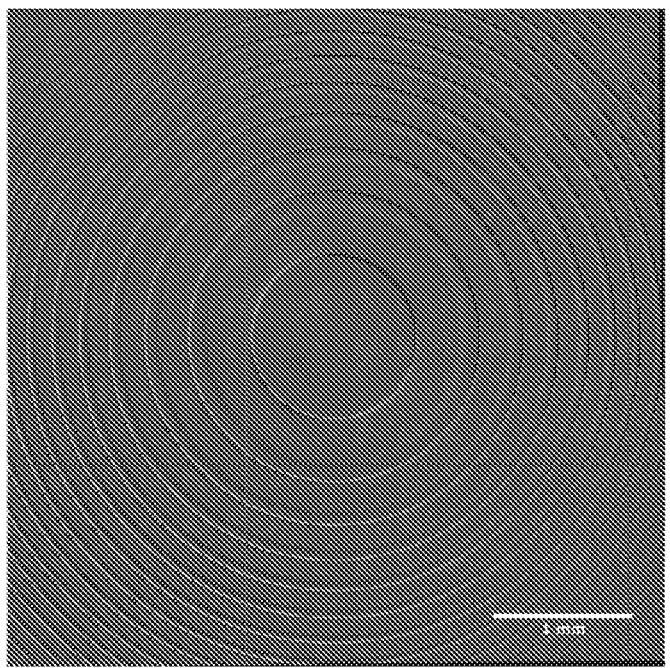
FIG. 7A
FIG. 7B

R¹ =

R² =

HIGH DYNAMIC RANGE TWO-STAGE PHOTOPOLYMERS

CROSS-REFERENCE TO RELATED APPLICATIONS

The present application is a 35 U.S.C. § 371 national stage application from, and claims priority to, International Application No. PCT/US2019/036375, filed Jun. 10, 2019, which claims priority under 35 U.S.C. § 119(e) to U.S. Provisional Application No. 62/682,659, filed Jun. 8, 2018, all of which are incorporated herein by reference in their entireties.

STATEMENT REGARDING FEDERALLY SPONSORED RESEARCH OR DEVELOPMENT

This invention was made with government support under grant numbers ECCS1307918 and DMR1310528 awarded by the National Science Foundation. The government has certain rights in the invention.

BACKGROUND OF THE INVENTION

Two-stage photopolymers are an ideal framework for designing materials capable of accessing a wide range of material properties (mechanical, thermal, optical, electrical etc.) on demand using light. A valuable implementation of the two stage paradigm is in designing recording materials (often referred to as holographic photopolymers) for appropriate refractive index (phase) structures using various optical exposure techniques (such as photolithography, direct laser write (DLW), two-photon lithography and holography) to generate a refractive index contrast ($\Delta n$) between the bulk material and the recorded feature(s). In particular, the advent of augmented reality (AR) devices has spurred a rising interest to use photopolymers to fabricate holographic optical elements (HOEs) capable of complex, yet high quality, optical functions with thin, light and flexible form factors.

Within the scope of formulating two-stage holographic photopolymers, the recordable $\Delta n$ is a function of the difference in refractive index of the writing polymer and the matrix ($n_{polymer} - n_{matrix}$) as well as the volume fraction of the initial writing monomer present in the material (Ø). However, the effective high refractive index substituents (such as heavy halogens or aromatics) have high molar refractions and low molar volumes, which are drastically different in structure to substituents of lower refractive index. Therefore, for a given matrix, there is typically a significant trade-off between increasing the refractive index of the writing monomer and its reduced solubility in the underlying matrix.

Recently, sequential and orthogonal two-stage thiol-X click chemistry systems achieving high solubility have been successfully demonstrated with simple process ability; however these formulations exhibited a low overall $\Delta n$ ($\leq 4.0 \times 10^{-3}$) primarily due to the low refractive index difference ($n_{polymer} - n_{matrix}$) associated with the presence of thiols in the stage 1 reactions. Similar issues of limited achievable $\Delta n$ are encountered with alternative photopolymer systems involving acrylamide writing monomers which have refractive indices similar to the binder, poly(vinyl alcohol). Further, the holographic composites such as nanoparticle-based photopolymers or liquid crystal photopolymers, whereby the nanoparticles or liquid crystals, acting as nonreactive higher refractive index species, migrate to the dark regions upon holographic exposure have also been explored. However, the intrinsic drawbacks of limited nanoparticle solubility and the slow reaction kinetics (>1 minute for $\Delta n$ development despite high recording intensities of 100-200 mW/cm$^2$) persist. The synthesis of high refractive index nanoparticles is also relatively cumbersome and arguably not a viable approach for mass use as recording materials.

Considering the aforementioned limitation of the existing recording materials, there is need in the art to develop recording materials that have high refractive index, fast reaction kinetics, and good solubility in the matrix/bulk. The present invention meets this need.

BRIEF SUMMARY OF THE INVENTION

In one embodiment, the invention provides a monomer of formula (I),

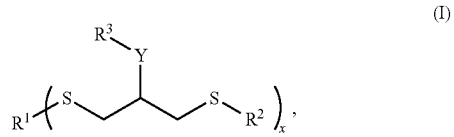

wherein Y, $R^1$, $R^2$, $R^3$, and x are as described elsewhere herein. The monomer of the invention exhibits a high refractive index of about 1.6, and shows good solubility in the matrix/bulk material, such as for example urethane, used in the fabrication of holograms.

In other embodiments, the invention provides a polymer comprising the monomer of formula (I). The polymer of the invention are photopolymers exhibiting a high refractive index of about 1.6, which is highly desirable for using the polymer in holographic applications.

BRIEF DESCRIPTION OF THE FIGURES

For the purpose of illustrating the invention, there are depicted in the drawings certain embodiments of the invention. However, the invention is not limited to the precise arrangements and instrumentalities of the embodiments depicted in the drawings.

FIG. 2A is a schematic of volume transmission holograms recording sinusoidal diffraction gratings of 1 μm fringe spacing with a peak recording intensity of 16 mW/cm$^2$ of a Gaussian laser beam with a 1/e$^2$ diameter of 4.3 mm. FIG. 2B is a schematic of photomask lithography using a 1" diameter Fresnel lens mask at an average recording intensity of 40 mW/cm$^2$. FIG. 2C is a schematic showing a direct laser write of an image pattern with a peak recording intensity of ~ 760 mW/cm$^2$ of a Gaussian beam with a 1/e$^2$ diameter of 10 μm.

FIG. 5A is a set of graphs showing representative diffraction efficiency vs. reconstruction angle scans for 40, 50 and 60 wt % BPTPA formulations with the corresponding fits to classical Kogelnik Coupled Wave theory. FIG. 5B is a graph comparing peak-to-mean Δn performance of TBPA against BPTPA as a function of writing monomer content. The grey dashed-outline box in the upper right hand corner reveals the realized and achievable Δn increase from the higher solubility writing monomer BPTPA.

FIGS. 7A-7B are images demonstrating refractive index gradient examples. Stitched DIC microscope images of (FIG. 7A) direct laser write of a bird pattern, (FIG. 7B) projection mask lithography of a 1-inch diameter Fresnel lens.

DETAILED DESCRIPTION OF THE INVENTION

Figure 1A:
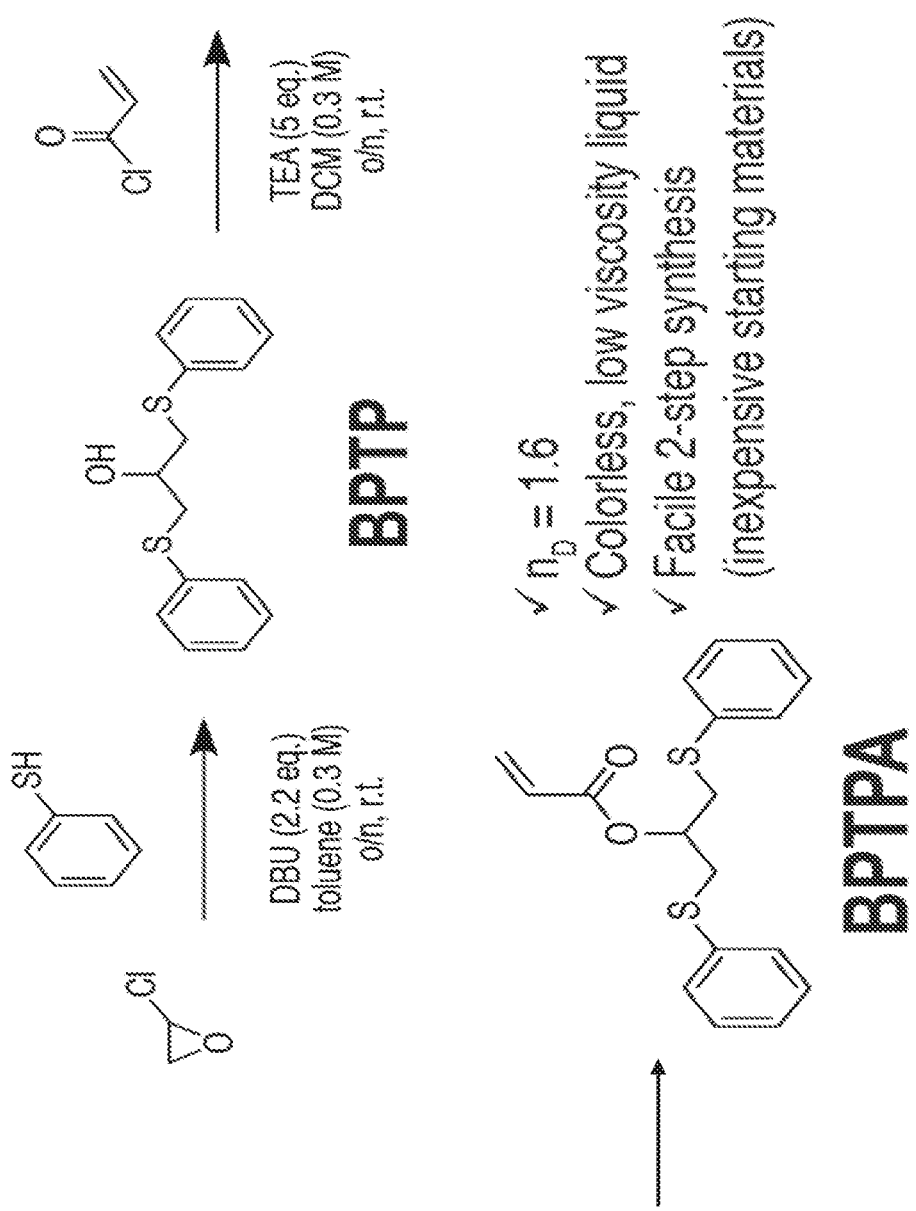
FIG. 1A is a scheme showing an overall synthetic route for novel acrylate writing monomer, 1,3-bis-(phenylthio)-2-propyl acrylate (BPTPA). The intermediate alcohol, 1,3-bis-(phenylthio)-2-propanol (BPTP), is synthesized by reaction with excess thiol under basic conditions to favor the bifunctional substitution after the thiol-epoxy ring opening reaction.

The present invention, in one aspect, relates to developing recording material for holographic application. Colorless, low viscosity, high refractive index ($n_D$=1.6 or higher) liquid acrylate monomer such as, for example, 1,3-bis-(phenylthio)-2-propyl acrylate (BPTPA), have been designed and synthesized herein. Solubility and refractive index experiments have been performed to evaluate viability of BPTPA as a two-stage holographic writing monomer against a reference, 2,4,6-tribromophenyl acrylate (TBPA).

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of 20% or +10%, more preferably ±5%, even more preferably ±1%, and still more preferably ±0.1% from the specified value, as such variations are appropriate to perform the disclosed methods.

As used herein, the term "click chemistry" refers to a chemical synthesis method that generates products quickly and reliably by joining small units under mild conditions.

Non-limiting examples include [3+2] cycloadditions, such as the Huisgen 1,3-dipolar cycloaddition; thiol-ene click reactions; Diels-Alder reaction and inverse electron demand Diels-Alder reaction; [4+1] cycloadditions between isonitriles (isocyanides) and tetrazines; nucleophilic substitution especially to small strained rings like epoxy and aziridine compounds; addition reactions to carbon-carbon double bonds like dihydroxylation or the alkynes in the thiol-yne reaction.

As used herein, the term "holography" refers to the science and the practice of making holograms. Typically, a hologram is a photographic recording of a light field, rather than an image formed by a lens. The holographic medium, i.e., the object produced by a holographic process (which itself may be referred to as a hologram) is usually unintelligible when viewed under diffuse ambient light. It is an encoding of the light field as an interference pattern of variations in the opacity, density, or surface profile of the photographic medium. When suitably lit, the interference pattern diffracts the light into an accurate reproduction of the original light field, and the objects that were in it exhibit visual depth cues such as parallax and perspective that change realistically with the relative position of the observer. That is, the view of the image from different angles represents the subject viewed from similar angles.

The term "monomer" refers to any discreet chemical compound that is polymerized when subjected to suitable conditions. Non-limiting examples of conditions that can cause a monomer to become polymerized include, electromagnetic radiation (e.g., UV, IR, and visible light) and thermal radiation (e.g., heating).

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "photoinitiator" refers to a molecule that creates reactive species (suh as for example, free radicals, cations or anions) when exposed to electromagnetic radiation such as UV or visible light.

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of the at least one functional group.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "reactive" as applied to thiol, azide, alkyne or alkene groups indicate that these groups under appropriate conditions may take part in one or more reactions as defined in this application.

As used herein, "step-growth polymerization" refers to a type of polymerization mechanism wherein bifunctional or multifunctional monomers react first to form dimers, then trimers, then eventually long chain polymers. In the event of multi-functional monomers, crosslinked polymers are produced.

As used herein, the term "thiol-click chemistry" refers to click chemistry wherein a thiol is one of the reactants.

As used herein, the term "thiol-ene reaction" refers to an organic reaction between a thiol monomer and an ene monomer. In certain embodiments, the ene monomer is an α,β-unsaturated ester, acid, sulfone, nitrile, ketone, amide, aldehyde, or nitro compound (Hoyle, et al., Angew. Chem. Intl Ed., 2010, 49(9):1540-1573); the thio-ene reaction involving such reactants is known as "thiol-Michael reaction."

As used herein, the term "thiol-ene polymerization" refers to polymerization wherein at least one thiol-ene reaction takes place.

As used herein, the term "alkyl", by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "cycloalkyl", by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl", employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1, 3-pentadienyl, 1, 4-pentadienyl, and the higher homologs and isomers. A functional group representing an alkene is exemplified by —$CH_2$—CH=$CH_2$.

As used herein, the term "alkynyl", employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene. Heteroalkylene substituents can a group consisting of the stated number of carbon atoms and one or more heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted", "substituted alkyl", "substituted cycloalkyl", "substituted alkenyl", "substituted alkynyl", "substituted alkylene", "substituted alkenylene" or "substituted alkynylene" means alkyl, cycloalkyl, alkenyl, alkynyl, alkylene, alkenylene, alkynylene as defined herein, substituted by one, two or three substituents selected from the group consisting of $C_1$-$C_{10}$ alkyl, halogen, =O, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof. In certain embodiments, the aryl group is phenyl. In other embodiments, the aryl group is naphthyl. In yet other embodiments, the aryl group is biphenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

Compounds

Monomers

In one embodiment, the invention provides a monomer of formula (I):

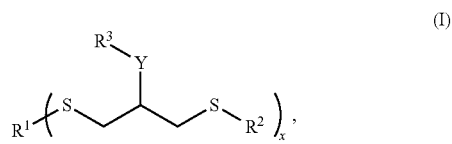

wherein, each instance of Y is independently O, S, or NH;

each instance of $R^1$ and $R^2$ is independently selected from the group consisting of optionally substituted $C_6$-$C_{15}$ aryl, optionally substituted $C_5$-$C_{18}$ heteroaryl, and $C_1$-$C_3$ alkyl optionally substituted with 1-6 independently selected $C_6$-$C_{10}$ aryl groups;

$R^3$ is selected from the group consisting of optionally substituted $C_2$-$C_{15}$ alkenyl, optionally substituted $C_2$-$C_{15}$ heteroalkenyl, optionally substituted $C_2$-$C_{15}$ alkynyl, optionally substituted $C_2$-$C_{15}$ heteroalkynyl, optionally substituted —C(=O)—$C_2$-$C_{15}$ alkenyl, optionally substituted —C(=O)—$C_2$-$C_{15}$ alkynyl, optionally substituted —C(=O)—$C_3$-$C_{10}$ cycloalkenyl, optionally substituted $C_3$-$C_{10}$ cycloalkenyl, and optionally substituted $C_3$-$C_{10}$ heterocycloalkenyl; and x is an integer ranging from 1 to 4.

In certain embodiments, $R^3$ is selected from the group consisting of

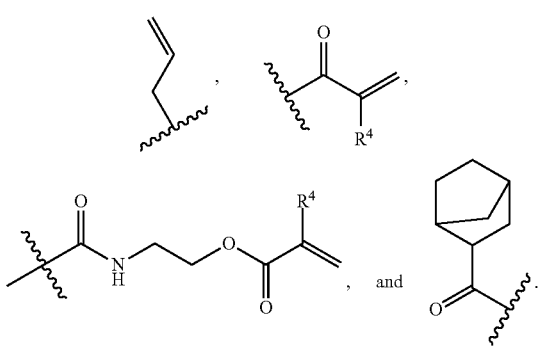

In certain embodiments, $R^4$ is selected from the group consisting of H and —$CH_3$.

In certain embodiments, $R^1$ and $R^2$ are each independently selected from the group consisting of

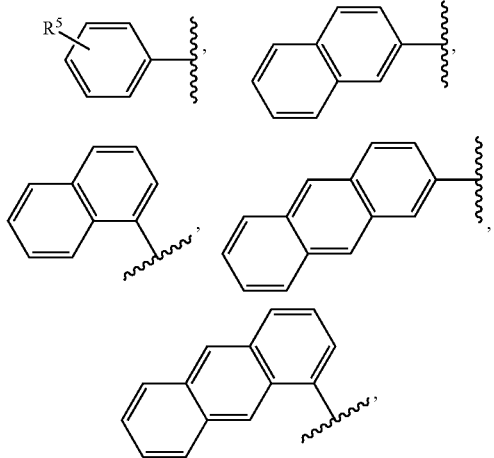

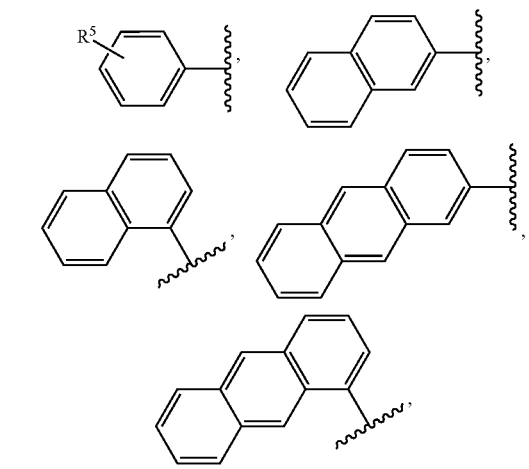

and and; and $R^5$ is selected from the group consisting of H, optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ hetero alkenyl, optionally substituted $C_2$-$C_6$ alkynyl, optionally substituted $C_2$-$C_6$ heteroalkynyl.

In certain embodiments, if x is 1 and $R^3$ is

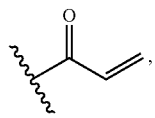 [SMILES: *C(=O)C=C]

then one of $R^1$ or $R^2$ is not phenyl.

In certain embodiments, $R^1$ selected from the group consisting of

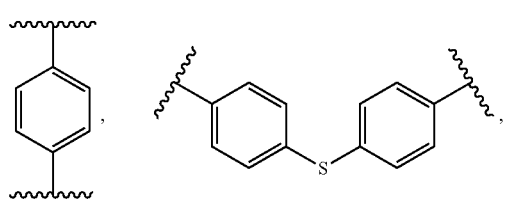 [SMILES: *c1ccc(*)cc1 ; *c1ccc(Sc2ccc(*)cc2)cc1]

and

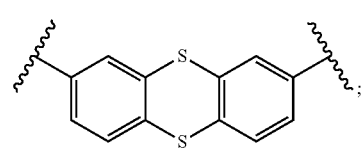 [SMILES: *c1ccc2c(c1)Sc1cc(*)ccc1S2]

each instance of $R^2$ is independently selected from the group consisting of

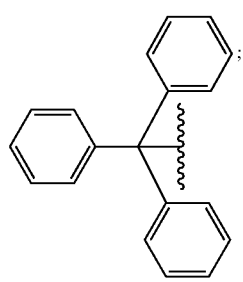 [SMILES: *C(c1ccccc1)(c1ccccc1)c1ccccc1]

$R^5$ is as described elsewhere herein; and x is 2.

In certain embodiments, $R^1$ and $R^2$ are each independently selected from the group consisting of

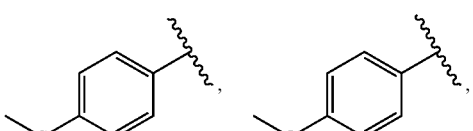

and

In certain embodiments the monomer is selected from the group consisting of

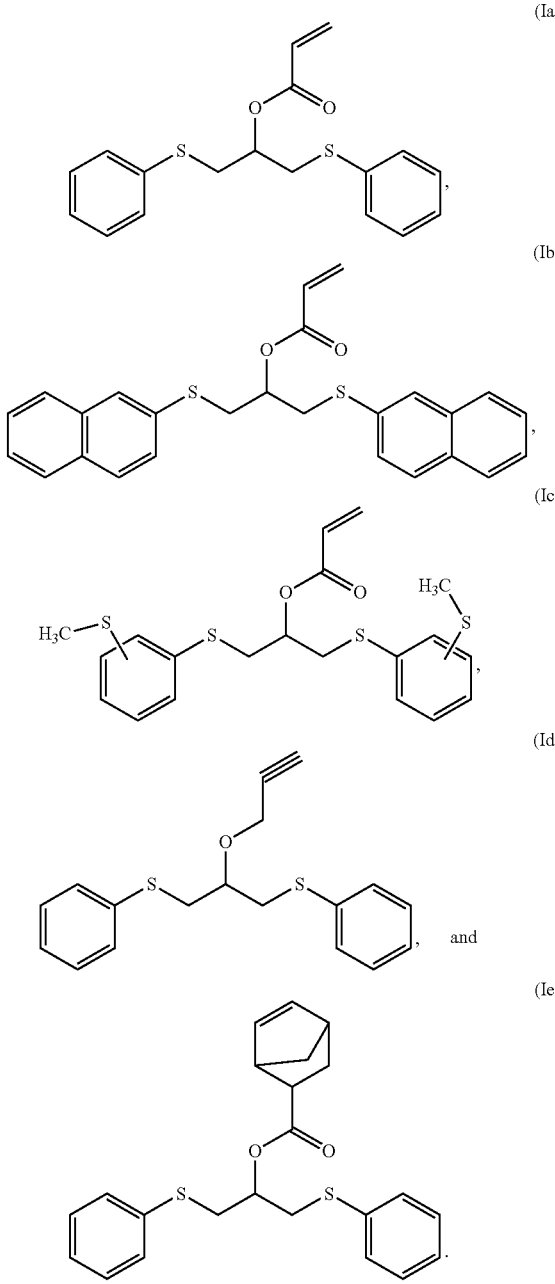

In certain embodiments, the monomer is selected from the group consisting of 1,3-bis(phenylthio)propan-2-yl acrylate, 1,3-bis(naphthalen-2-ylthio)propan-2-yl acrylate, (2-(prop-2-yn-1-yloxy)propane-1,3-diyl)bis(phenylsulfane), and 1,3-bis(phenylthio)propan-2-yl bicyclo[2.2.1]hept-5-ene-2-carboxylate.

In certain embodiments, the monomer has a refractive index of greater than about 1.6. In certain embodiments, the monomer has a refractive index of about 1.62. In certain embodiments, the monomer has a refractive index of about 1.64. In certain embodiments, the monomer has a refractive index of about 1.66. In certain embodiments, the monomer has a refractive index of about 1.68.

In certain embodiments, the monomer is photopolymerizable.

In certain embodiments, the monomer is selected from the group consisting of 1,3-bis(phenylthio)-2-propyl acrylate (BPTPA), 1,3-bis((methylthio)phenylthio)-2-propyl acrylate (BMTPTPA), and 1,3-bis(naphthylthio)-2-propyl acrylate (BNTPA).

In certain embodiments the monomers of the invention are selected from the group consisting of 1,4-benzene dithiol-based diallyl ether (BDTDAE), 4,4'-thiobisbenzenethiol-based diallyl ether (TBTDAE) and 2,7-thianthrene dithiol-based diallyl ether (TDTDAE).

In certain embodiments, solubility and refractive index experiments have been performed to evaluate viability of BPTPA as a two-stage holographic writing monomer against a reference, 2,4,6-tribromophenyl acrylate (TBPA). Monomer swelling studies of a urethane matrix showed a solubility improvement of around 50% as compared to TBPA in addition to a moderately higher refractive index increase per unit concentration of writing monomer. Crucially, it was demonstrated that the optically clear films containing twice the amount of writing monomer are possible with BPTPA (60 wt %) when compared to TBPA, making peak-to-mean Δn~0.029 accessible without any discernable optical deficiencies. The capabilities and versatility of BPTPA formulations are demonstrated through functional examples of refractive index structures at varying length scales through direct laser write (DLW) of an intricate pattern, projection mask lithography of a Fresnel lens, and transmission holograms.

Polymers

In another embodiment, the invention provides a polymer comprising the monomer of formula (I).

Figure 1B:
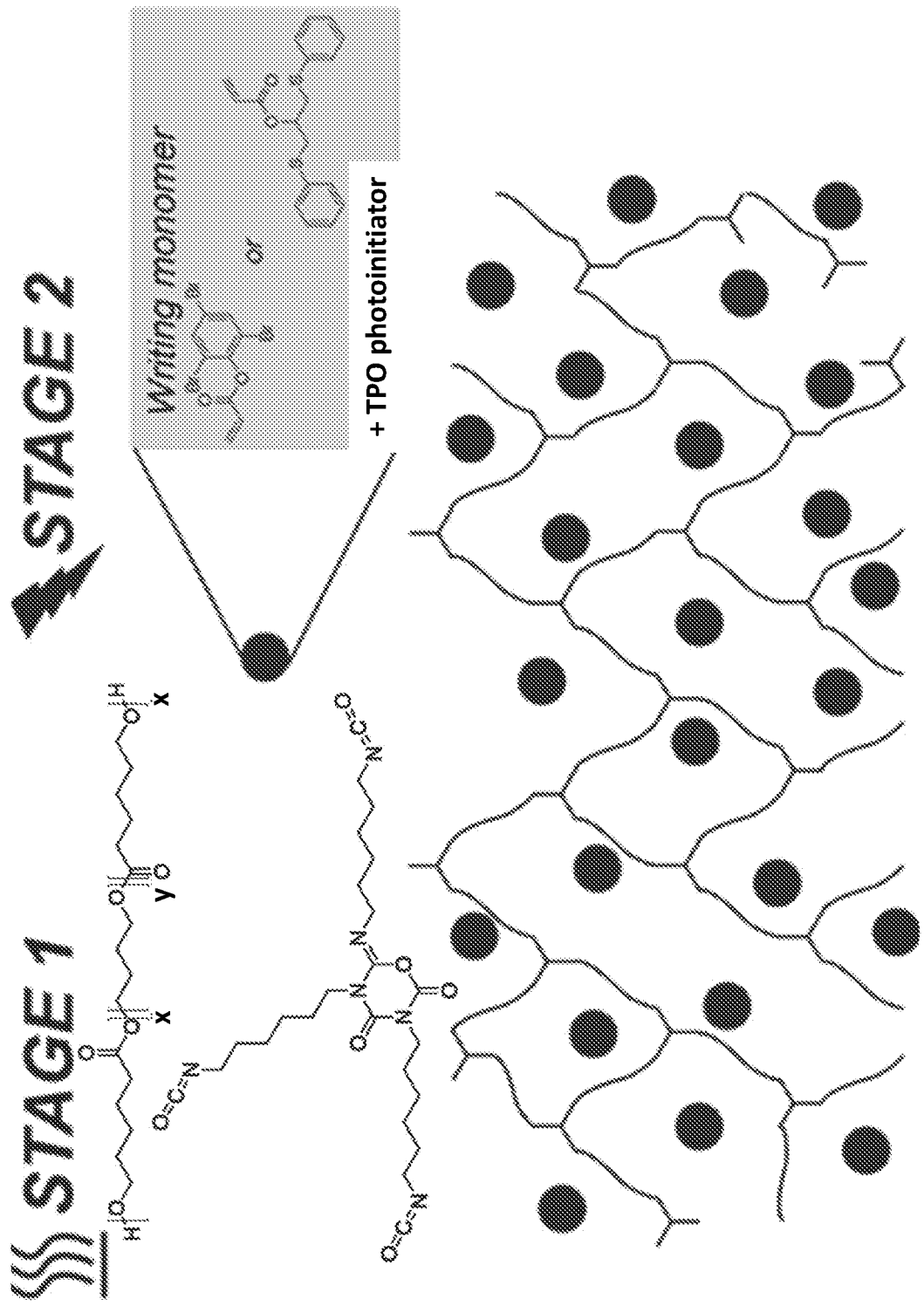
FIG. 1B is a schematic illustration of two-stage holographic photopolymer formulations. The stage 1 alcohol-isocyanate network is thermally cured at 70° C. overnight with the dissolved writing chemistry (TPO photoinitiator with either 2,4,6-Tribromophenyl acrylate (TBPA) or BPTPA) available for 405 nm recording.

In certain embodiments, the polymer of the invention is a two-stage holographic photopolymer used for designing recording material to fabricate holographic optical elements (HOEs) capable of complex, yet high quality, optical functions. The general scheme of two stage photo polymerization involves an initial thermal cure of a solid rubbery matrix (stage 1), typically of lower refractive index (n<1.5), as shown in FIG. 1B. This matrix acts as a framework through which dissolved species (writing monomer and photoinitiator) freely diffuse and undergo photopolymerization during a subsequent patterned irradiation step. This patterned light exposure spatially controls the polymerization (stage 2) according to the light intensity profile, consuming the reactive monomer species in the exposed regions and inducing mass transport of additional monomer from the unexposed regions into the exposed regions to enhance the developing refractive index structure. In refractive index imaging, a pattern of varying refractive indices is created within the material used to record the image. This pattern is commonly referred to as a phase hologram. When light is subsequently transmitted through, or directed onto the surface of the recording medium, the phase of the light is modulated by the pattern of refractive indices.

In certain embodiments, the polymer of the invention has a high refractive index equal to or greater than about 1.6. In certain embodiments, the polymer has a refractive index equal to or greater than about 1.62. In certain embodiments, the polymer has a refractive index equal to or greater than about 1.63. In certain embodiments, the polymer has a refractive index equal to or greater than about 1.64. In certain embodiments, the polymer has a refractive index equal to or greater than about 1.65. In certain embodiments, the polymer has a refractive index equal to or greater than about 1.66. In certain embodiments, the polymer has a refractive index equal to or greater than about 1.67. In certain embodiments, the polymer has a refractive index equal to or greater than about 1.68. In certain embodiments, the polymer has a refractive index equal to or greater than about 1.69. In certain embodiments, the polymer has a refractive index equal to or greater than about 1.70. In certain embodiments, the polymer has good solubility in the matrix.

In certain embodiments, the invention further provides a thiol-capped oligomer of formula (II):

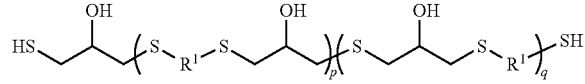

(II)

wherein,

R$^1$ is selected from the group consisting of optionally substituted C$_6$-C$_{18}$ aryl, optionally substituted C$_5$-C$_{18}$ heteroaryl, and C$_1$-C$_3$ alkyl optionally substituted with 1-6 independently selected C$_6$-C$_{10}$ aryl groups;

p is any integer ranging from 2 to 200; and q is an integer ranging from 0 to 200.

Compositions

In certain embodiments, the invention provides a composition comprising the monomer of the invention, a matrix having a refractive index of less than about 1.5; and at least one photoinitiator.

In certain embodiments, the matrix comprises urethane or polyurethane. Other suitable matrix materials include polyether based polyurethane matrices containing trifunctional polypropylene oxides as described in, for example, U.S. Pat. Nos. 6,743,552, 6,765,061 and 6,780,546. Other suitable polyurethane-based matrix materials include the polyurethanes incorporating polyether polyols as described in U.S. Pat. No. 8,361,678.

In certain embodiments the photoinitiator is selected from the group consisting of acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4'-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide (TPO), Ethyl (2,4,6-trimethylbenzoyl) phenyl phosphinate, lithium phenyl-2,4,6-trimethylbenzoylphosphinate,

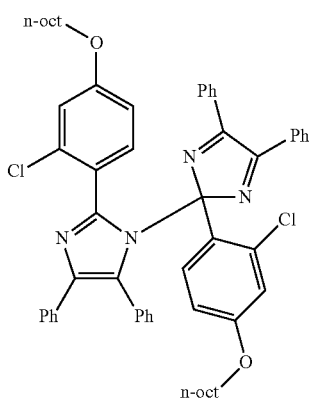

and

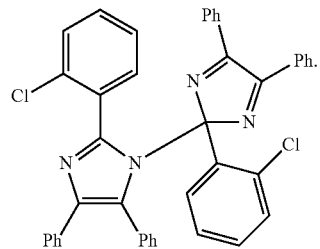 [SMILES: Clc1ccccc1-c1nc(-c2ccccc2)c(-c2ccccc2)n1C1(c2ccccc2Cl)N=C(c2ccccc2)C(c2ccccc2)=N1]

In certain embodiments, the composition is thermally cured at the temperature of about 50° C. to about 90° C. In certain embodiments, the composition is thermally cured at a temperature of about 55° C. In certain embodiments, the composition is thermally cured at a temperature of about 60° C. In certain embodiments, the composition is thermally cured at a temperature of about 65° C. In certain embodiments, the composition is thermally cured at a temperature of about 70° C. In certain embodiments, the composition is thermally cured at a temperature of about 75° C. In certain embodiments, the composition is thermally cured at a temperature of about 80° C. In certain embodiments, the composition is thermally cured at a temperature of about 85° C. In certain embodiments, the composition is thermally cured at a temperature of about 90° C.

In certain embodiments, the composition is further photopolymerized using UV radiation having wavelength ranging from about 390 nm to about 410 nm. In certain embodiments, the composition is photopolymerized using UV radiation having wavelength of about 390 nm. In certain embodiments, the composition is photopolymerized using UV radiation having wavelength of about 395 nm. In certain embodiments, the composition is photopolymerized using UV radiation having wavelength of about 400 nm. In certain embodiments, the composition is photopolymerized using UV radiation having wavelength of about 405 nm. In certain embodiments, the composition is photopolymerized using UV radiation having wavelength of about 410 nm.

Within the scope of formulating two-stage holographic photopolymers, the recordable Δn is a function of the difference in refractive index of the writing polymer and the matrix ($n_{polymer}$–$n_{matrix}$). For a photopolymer to be a good candidate for holographic application, the polymer must possess high refractive index and must be highly soluble in the matrix. A higher Δn also enables the manufacture of gradient refractive index lenses with greater focusing power as well as having the capacity to record waveguides with tighter bend radii. In terms of device performance, this translates to improved specifications such as wider field of views, higher information densities, lower power read-out sources, etc.

In certain embodiments, the difference in the refractive index (Δn) of the matrix and the polymer is greater than about 0.02. In certain embodiments the Δn is about 0.022. In certain embodiments the Δn is about 0.024. In certain embodiments the Δn is about 0.026. In certain embodiments the Δn is about 0.028. In certain embodiments the Δn is about 0.030. In certain embodiments the Δn is about 0.032. In certain embodiments the Δn is about 0.034.

In one specific embodiment, writing monomer are possible with BPTPA and the matrix is urethane matrix, the Δn~0.029.

In certain embodiments, the compositions described herein are useful for making holograms.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials

Commercially available reagents were used without further purification. Thiophenol, epichlorohydrin and butylated hydroxytoluene (BHT) free radical stabilizer were purchased from Alfa Aesar. 1,8-Diazabicyclo[5.4.0]undec-7-ene (DBU) was purchased from Chem-Impex International. 4-dimethylaminopyridine (DMAP) was purchased from Oakwood Chemical. Reagent-grade triethylamine ($Et_3N$) was purchased from Fisher Scientific.

Acryloyl chloride and polycaprolactone-block-polytetrahydrofuran-block-polycaprolactone, (average $M_n$ 2000) were purchased from Sigma Aldrich. The photoinitiator, diphenyl(2,4,6-trimethylbenzoyl)phosphine oxide (TPO), was purchased from TCI America. Desmodur N3900 polyisocyanate was donated by Covestro AG (formerly Bayer MaterialScience).

Synthesis of 1,3-bis-(phenylthio)-2-propanol (BPTP)

To a 250 mL round-bottomed flask equipped with a magnetic stir bar, 16 mL of thiophenol (157 mmol, 2.2 equiv.) was stirred with 23 mL of DBU (154 mmol, 2.2 equiv.) in 230 mL of toluene (0.3 M, w.r.t epichlorohydrin) for 10 minutes. Following this, 5.5 mL of epichlorohydrin (70.3 mmol, 1.0 equiv.) was added dropwise. The reaction vessel was allowed to stir at room temperature for 16 hrs. After this period, the volatiles were removed under reduced pressure and the residue was then diluted with DCM (dichloromethane) and washed with 1 M HCl (100 mL), distilled water (100 mL) and brine (50 mL). The combined organic extracts were dried over anhydrous $Na_2SO_4$, filtered and concentrated under reduced pressure. The crude product was purified by silica-gel column chromatography using 20% EtOAc in hexane as eluent to yield 17.1 g of a colorless, low viscosity liquid. (88% yield). $^1H$ NMR (400 MHz, $CDCl_3$) δ 7.36-7.33 (m, 4H), 7.29-7.24 (m, 4H), 7.22-7.18 (m, 2H), 3.86-3.79 (m, 1H), 3.20 (dd, J=13.8, 5.0 Hz, 2H), 3.05 (dd, J=13.8, 7.2 Hz, 2H); $^{13}C$ NMR (101 MHz, $CDCl_3$, 25° C.): δ 135.1, 129.9, 129.1, 126.7, 68.2, 40.1;

Synthesis of Acrylate Writing Monomer, 1, 3-bis-(phenylthio)-2-propyl acrylate (BPTPA)

To a 250 mL round-bottomed flask equipped with a magnetic stir bar, 10 g of BPTP (36.2 mmol, 1.0 equiv.), 25.2 mL of $Et_3N$ (180.9 mmol, 5 equiv.), 0.4 g of BHT (1.81 mmol, 0.05 equiv.) were diluted with 120 mL of DCM (0.3 M with respect to BPTP) and stirred for 10 minutes under an argon atmosphere. The clear solution was cooled to 0° C. and 4.4 mL of acryloyl chloride (54.3 mmol, 2.2 equiv.) was added dropwise to the flask under Ar atmosphere followed by 0.4 g of DMAP (3.6 mmol, 0.1 equiv.). The reaction mixture was allowed to stir at room temperature for 16 hr. After this period, the volatiles were removed under reduced pressure and the residue was diluted with DCM (250 mL) and washed with 1 M HCl (100 mL), distilled water (100 mL) and brine (50 mL). The combined organic extracts were dried over anhydrous $Na_2SO_4$, filtered and concentrated under reduced pressure. The crude product was purified by silica-gel column chromatography using 20% EtOAc in hexane as eluent to yield the title compound BPTPA as a colorless, low viscosity liquid. (84% yield). $^1H$ NMR (400 MHz, $CDCl_3$) δ 7.38-7.35 (m, 4H), 7.28-7.24 (m, 4H), 7.20-7.16 (m, 2H), 6.27 (dd, J=17.3, 1.4 Hz, 1H), 5.94 (dd, J=17.3, 10.5 Hz, 1H), 5.76 (dd, J=10.5, 1.4 Hz, 1H), 5.18 (p, J=5.9 Hz, 1H), 3.29 (dd, J=5.9, 3.3 Hz, 4H); $^{13}C$ NMR (101 MHz, $CDCl_3$, 25° C.): δ 165.3, 135.2, 131.4, 129.9, 129.0, 127.9, 126.6, 72.0, 36.3; Nuclear magnetic resonance (NMR) NMR spectra were recorded on a Bruker Avance-III 400 NMR spectrometer at 25° C. in chloroform-d. All chemical shifts are reported in ppm relative to chloroform solvent peak (δ=7.26 ppm).

Refractive Index Measurements

The refractive indices of liquid samples were measured using an Abbe refractometer at the sodium-d line (589.3 nm) at room temperature. The refractive index of polymeric films was measured using a Metricon 2010/M prism coupler at a wavelength of 633 nm under ambient conditions.

Writing Monomer Swelling in Urethane Matrix

Half-inch diameter discs were punched out of 250 µm urethane films and their dry weights ($w_i$) measured. They were then individually placed in 4 mL vials containing either—a) 20 wt % TBPA in solvent, b) 20 wt % BPTPA in solvent or c) 100% solvent. The relatively nonvolatile solvents chosen were hexane and heavy mineral oil. After 1 week, the surface of each disc was patted dry with weighing paper and their equilibrium weights ($w_f$) measured.

Two-Stage Photopolymer Recording Film Preparation

Two-stage photopolymer film samples were prepared by premixing the acrylate writing monomer (either TBPA or BPTPA) measured at a set weight percentage (relative to the entire formulation) with 1-3 wt % TPO photoinitiator (based on writing monomer concentration) and the difunctional polyol in a 4 mL vial equipped with a magnetic stir bar until homogenous. A stoichiometric amount (OH:NCO=1:1) of Desmodur N3900 trifunctional isocyanate was added to the vial and stirred. The resin was cast onto clean 1×1.5" glass slides and sandwiched with a corresponding glass slide or cover slip (Fisher Scientific) using binder clips with PET spacers of defined thicknesses (15, 25 & 250 μm) lining the perimeter to control the thickness. Samples were covered in aluminum foil and allowed to cure overnight in an oven at 70° C. Acrylate reactivity was confirmed via FTIR to be negligible throughout this thermal process. A representation of the two-stage holographic photopolymers is illustrated in FIG. 1B.

Fourier Transform Infrared Spectroscopy (FTIR)

Fourier transform infrared spectroscopy was used to monitor the polymerization of the acrylate double bonds. A Thermo Scientific Nicolet 6700 FTIR spectrometer was electronically synchronized with a 405 nm LED source (Thorlabs) using a myDAQ device (National Instruments), allowing for monitoring of the acrylate peak at 814 $cm^{-1}$ with a timed and defined illumination at 16 $mW/cm^2$. Optically thin samples were prepared between two salt (NaCl) plates using 15 μm spacers. The stage 1 to stage 2 acrylate conversion ($c_{acrylate}$) was monitored using a series scan, integrating over the range 790-830 $cm^{-1}$ where $A_{initial}$ is the area of the unconsumed acrylate peak, and $A_{final}$ is the area under the acrylate peak after the stage 2 reaction.

$$C_{acrylate} = \left(1 - \frac{A_{final}}{A_{initial}}\right) * 100\%$$

Holographic Recording

Figure 2A:
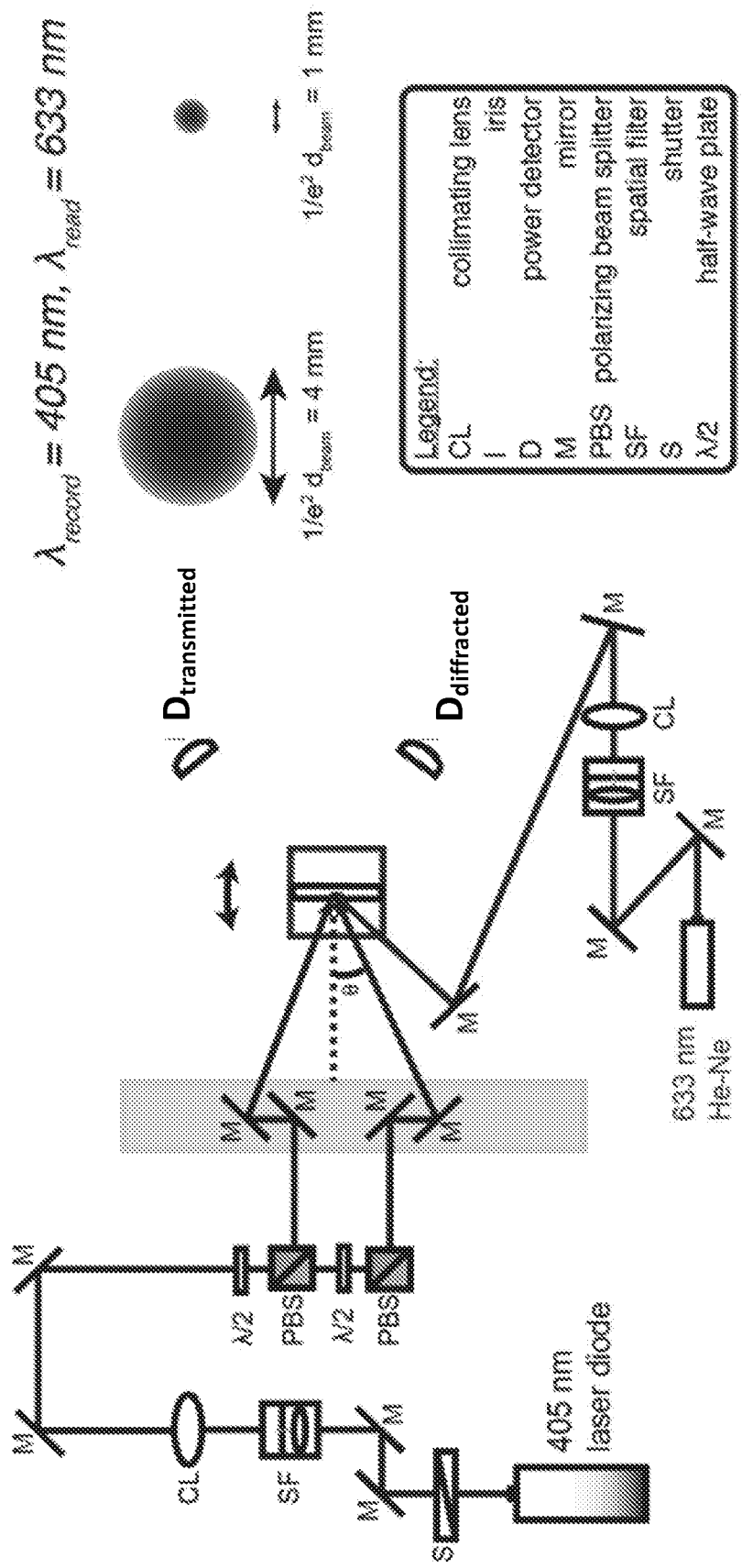
FIGS. 2A-2C are optical recording schematics for systems used to record the compositions of the invention with 405 nm light.

A two-beam interference setup shown in FIG. 2A was used to record volume transmission holograms with a spatially filtered wavelength stabilized 405 nm laser diode (Ondax, 40 mW). Both recording beams ($1/e^2$ intensity diameter of 4.3 mm) were power matched to give a total recording intensity of ~16 $mW/cm^2$. The beams were interfered at an external recording half-angle of 11.2° to produce a sinusoidal interference pattern with a fringe spacing of ~1 μm. A 633 nm He—Ne laser (Thorlabs), aligned approximately at the Bragg reconstruction angle, was used as a read beam to nondestructively probe the hologram formation throughout the recording process. Each recording exposure is initially monitored for 300 s, then followed by a sample rotation from 15° to −15° at an angle increment of 0.05°. The optical power at both of the two detectors was measured throughout the experiment. The diffraction efficiency of each recorded hologram was calculated by taking the quotient of the diffracted power ($P_d$) to the total power (transmitted+diffracted), $DE=I_d/(I_d+I_t)$. The diffraction efficiency vs. angle profile was fitted to Kogelnik coupled wave theory[34] to obtain a peak-to-mean Δn and thickness (d).

Photolithography Mask Exposure

Figure 2B:
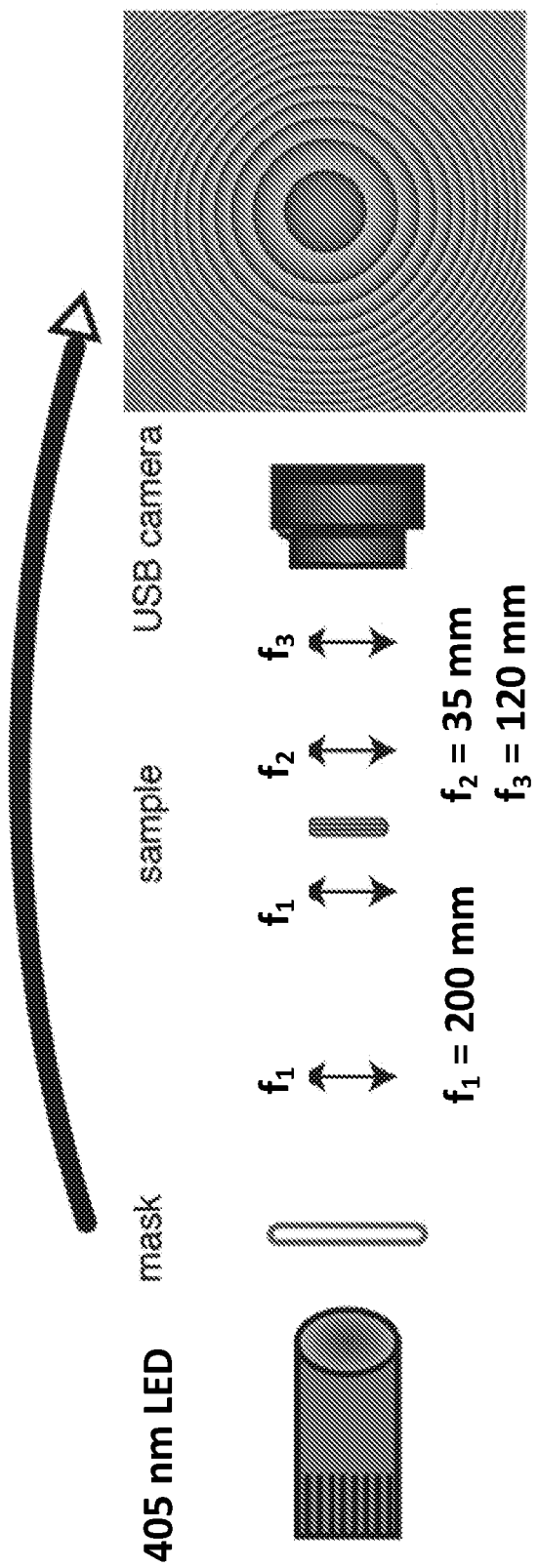

A projection lithography setup employing a 405 nm LED (Thorlabs—M405L3-C5) was used to expose a 1" diameter Fresnel lens (1.5 diopter) pattern on a greyscale halftone chrome mask (Toppan Mask) as illustrated in FIG. 2B.

Direct Laser Write

Figure 2C:
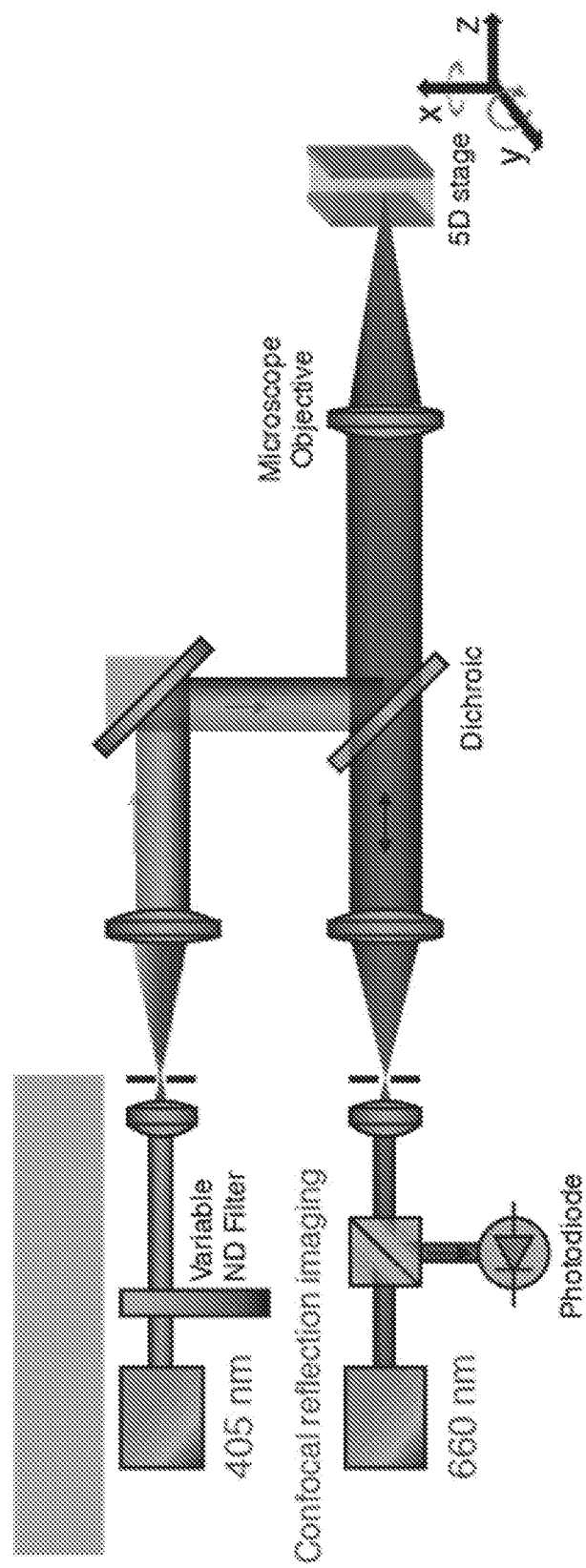

A 405 nm continuous wave laser with a focused spot ($1/e^2$ intensity diameter of 13 μm) is used to record isolated or continuous refractive index structures. The sample is mounted on a 5-axis stage that controls both tip/tilt and xyz motion, while a co-aligned confocal reflection microscope operating at 660 nm is used to align the sample as shown in FIG. 2C.

Example 1: Monomer Structure and Synthesis

High Δn two-stage holographic materials were made via an efficient writing monomer capable of a high refractive index after photopolymerization and significant loading into the matrix. This was achieved through the design of a novel writing monomer capable of increased solubility in the urethane matrix without sacrificing refractive index. High refractive index groups were incorporated via linker units to attach with the polymerizing functionality. Previous work has used alkyl chain linker units which reduce the overall refractive index of the monomer and polymer. To achieve this structure synthetically without the typical drawback in refractive index, a thiol-epoxy ring-opening reaction was employed using a relatively high refractive index thiol, thiophenol (reported $n_D$=1.588), and a substrate capable of further addition after the epoxide ring-opening, epichlorohydrin. The reaction was carried out with excess thiol under basic conditions so that after the initial ring opening reaction of the epichlorohydrin, the chloro-substituted alcohol intermediate (1-chloro-3-(phenylthio)-2-propanol) that formed was able to further react with thiophenol to yield the desired symmetric diphenylthio-substituted secondary alcohol, 1,3-bis(phenylthio)-2-propanol (BPTP), in a one-pot synthesis reaction. This molecular structure comprised advantageous characteristics for both refractive index and solubility. As outlined by the rearranged Lorentz-Lorenz equation, $$n = \sqrt{\frac{1 + 2\left(\frac{[R]}{V}\right)}{1 - \left(\frac{[R]}{V}\right)}}$$

where n is the refractive index, [R] is the molar refraction and V is the molar volume. In BPTPA, the phenyl ($N_A$=25.463), sulfur and tertiary carbon moieties present are known high refractive index substituents with a high molar refraction relative to molar volume.

In terms of solubility, the flexible thioether linkages are known to freely form random molecular orientations and thus suppress packing between polymer chains. This linker unit is also especially beneficial for imparting a high refractive index in terms of sulfur content (21% for BPTPA) as well as to improve the solubility of the writing monomer/polymer within the polymer matrix. This behavior is evident by the measured refractive index of 1.62 (Abbe refractometer at 589.3 nm) for the colorless, low viscosity liquid BPTP precursor. Consistent properties are maintained even after the acylation reaction with acryloyl chloride which results in a colorless, low viscosity liquid with a refractive index of 1.6 (Abbe). The neat photopolymerized acrylate film using 1 mol % TPO registered a refractive index of 1.627 via prism coupler measurements at 633 nm.

BPTPA was tested against a reference high refractive index writing monomer, 2,4,6-Tribromophenyl acrylate (TBPA). Given their comparable molecular weights, comparisons were done at equivalent weight percent compositions at 10 wt % increments. A solubility limitation at 50 wt % was encountered during formulation preparation whereby the TBPA monomer did not dissolve in the polyol to give a homogenous and transparent resin. In contrast, BPTPA formulations containing up to 60 wt % writing monomer was successfully prepared.

Example 2: Solubility of Writing Monomer in Urethane Matrix

To assess the solubility capabilities of the writing monomer in a urethane matrix, the equilibrium mass uptake of monomer in a non-solvent (mineral oil) by the urethane matrix (Table 1) was determined by measuring initial ($W_i$) and final weight ($W_f$). Approximately 50% more writing monomer ($W_f/W_i$) could be loaded into the matrix with BPTPA compared to TBPA. The quotient of the mass uptake of writing monomer ($W_f-W_i$) with the final weight of swollen matrix ($W_f$) was calculated to give a theoretical maximum loading of writing monomer (in wt %).

TABLE 1

Swelling-writing monomer mass uptake by the neat polymeric urethane matrix.

| Neat matrix | $W_f/W_i{}^a$ | $\Phi_{theoretical}$ (wt %) [b] |
|---|---|---|
| TBPA | 1.94 ± 0.07 | 45 ± 2 |
| BPTPA | 2.94 ± 0.06 | 63 ± 1 |
| Control (no writing monomer) | 1.03 ± 0.01 | — |

[a] The ratio of the measured final weight ($W_f$) of the sample to its initial weight ($W_i$) was calculated.
[b] Theoretical maximum loading (in wt %) was calculated by taking the ratio of the amount of mass uptake to its final weight, i.e. $\phi = (W_f - W_i)/W_f * 100\%$

Example 3: Refractive Index of Two-Stage Formulations

Figure 3:
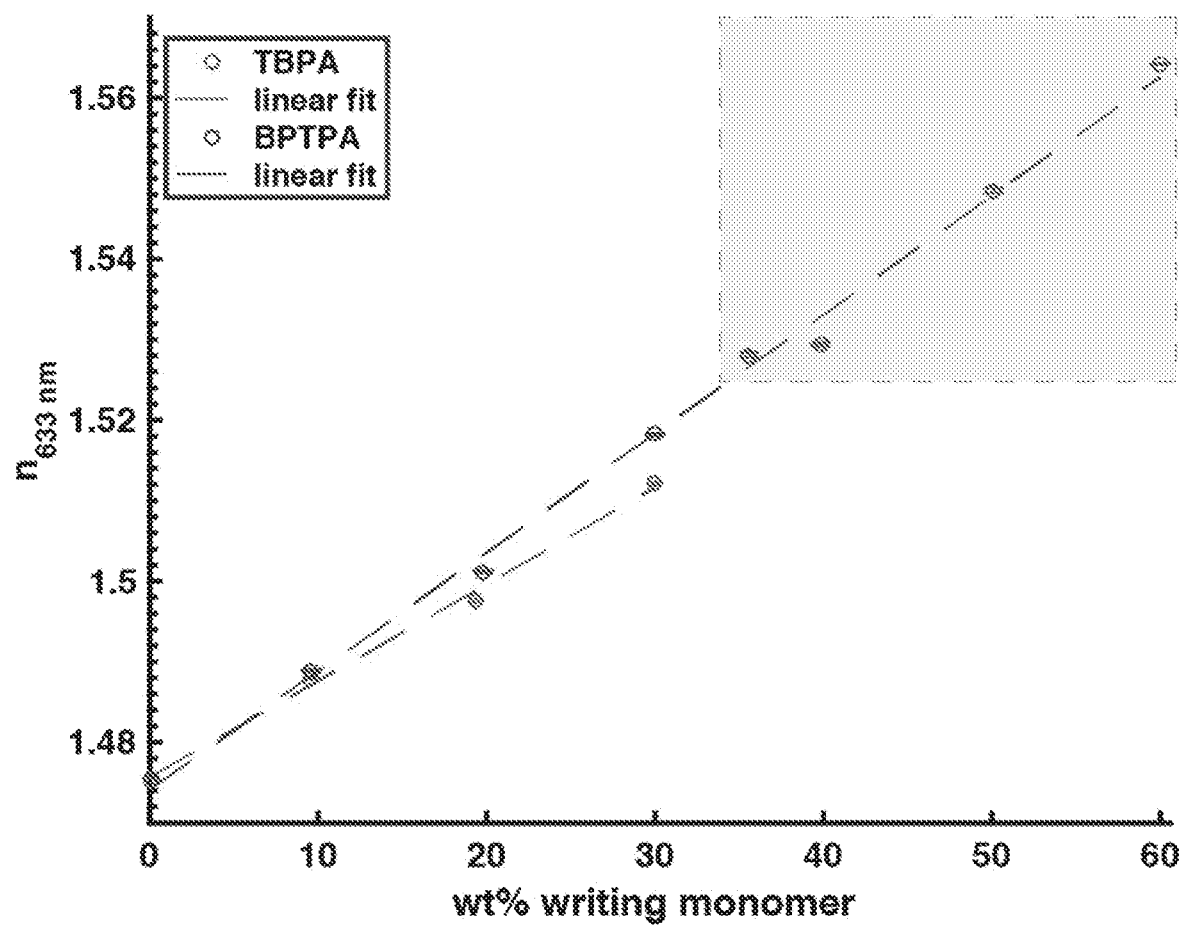
FIG. 3 is a graph of final (stage 2) refractive indices of two-stage formulations for TBPA (lower line) and BPTPA (upper line) as a function of writing monomer content in weight percent. The dashed-outline box in the upper right hand corner specifies the accessible region for refractive index increase due to a higher solubility writing monomer.

To determine the expected refractive index increase per unit of writing monomer present, the refractive indices of formulations containing varying amounts of writing monomer were measured in their stage 1 and stage 2 (after UV flood exposure) state as shown in FIG. 3. As shown from the gradients of the linear fits for both stage 1 and 2, BPTPA demonstrated a higher refractive index contrast increase per unit of writing monomer concentration (i.e. Δn/[M]). Using the gradient values for the linear fit equations, this Δn/[M] increase was estimated to be approximately 20%. Without intending to be limited to any particular theory, assuming both monomers react similarly in rate and final conversion, a marginally higher Δn structure would be expected at equivalent monomer concentrations. The ability to increase writing monomer loading extended the refractive index contrast ($n_{photopolymer}-n_{matrix}$) as shown by the dashed grey box inset of FIG. 3.

Example 4: Recording Kinetics

Figure 4A:
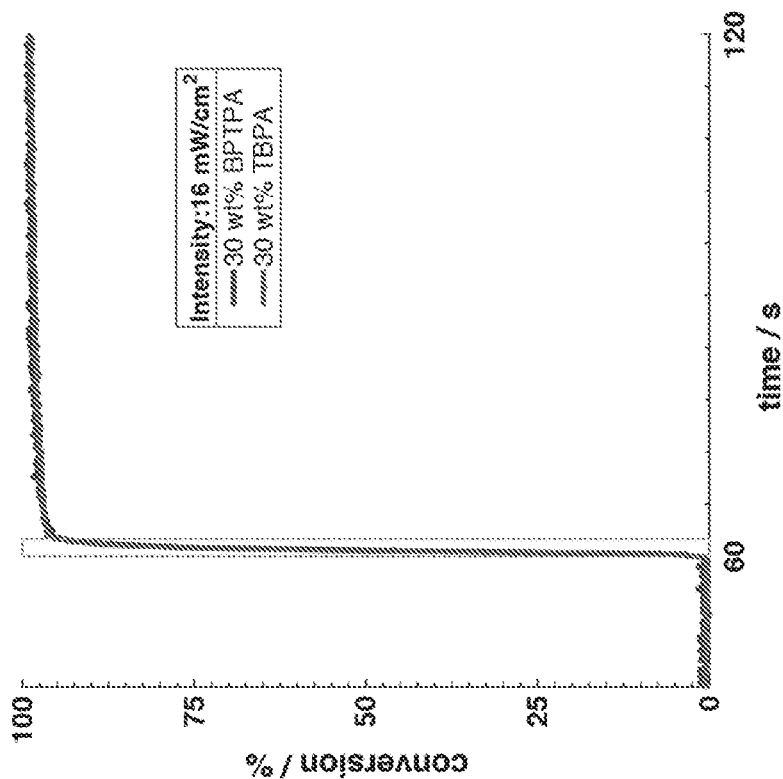
FIGS. 4A-4B are graphs showing real-time FTIR photopolymerization double bond conversion kinetics for the (FIG. 4A) neat acrylate (TBPA lower line; BPTPA upper line) homopolymerization with 1 mol % TPO using triggered 405 nm LED irradiation (20 s at 16 mW/cm$^2$) at the 60 s mark, and (FIG. 4B) acrylate homopolymerization of 30 wt % writing monomer (TBPA; BPTPA) formulation with 10 mol % TPO using triggered 405 nm LED irradiation (2 s at 16 mW/cm$^2$) at the 60 s mark.
Figure 4B:
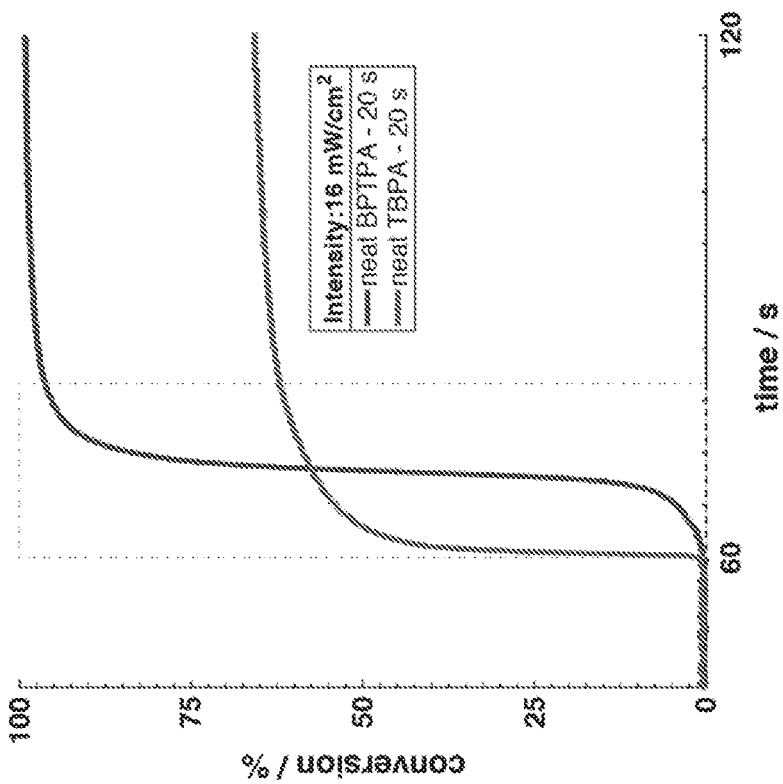

The photopolymerization reactivity of BPTPA was assessed neat and as a stage 2 photopolymerization using 30 wt % writing monomer via real-time FTIR spectroscopy. FIG. 4A shows that while TBPA had an almost instantaneous consumption of double bonds upon irradiation, it distinctly reached a plateau of around 65% conversion due to vitrification. In the case of neat BPTPA, however, it had a slower initial rate but did reach quantitative conversion within the exposure time of 20 seconds. Without intending to limited to any particular theory, this distinct polymerization kinetics profile is attributed to the lower viscosities throughout the polymerization of BPTPA. When these writing monomers are used in two-stage formulations, FIG. 4B shows that they both are indistinguishable in reactivity rates or final conversion (both quantitative). Therefore, the FTIR data suggests that BPTPA is at least comparable if not preferred to TBPA for its ability to go to full conversion at higher writing monomer loadings.

Example 5: Holographic Recording (Transmission Gratings)

Figure 5A:
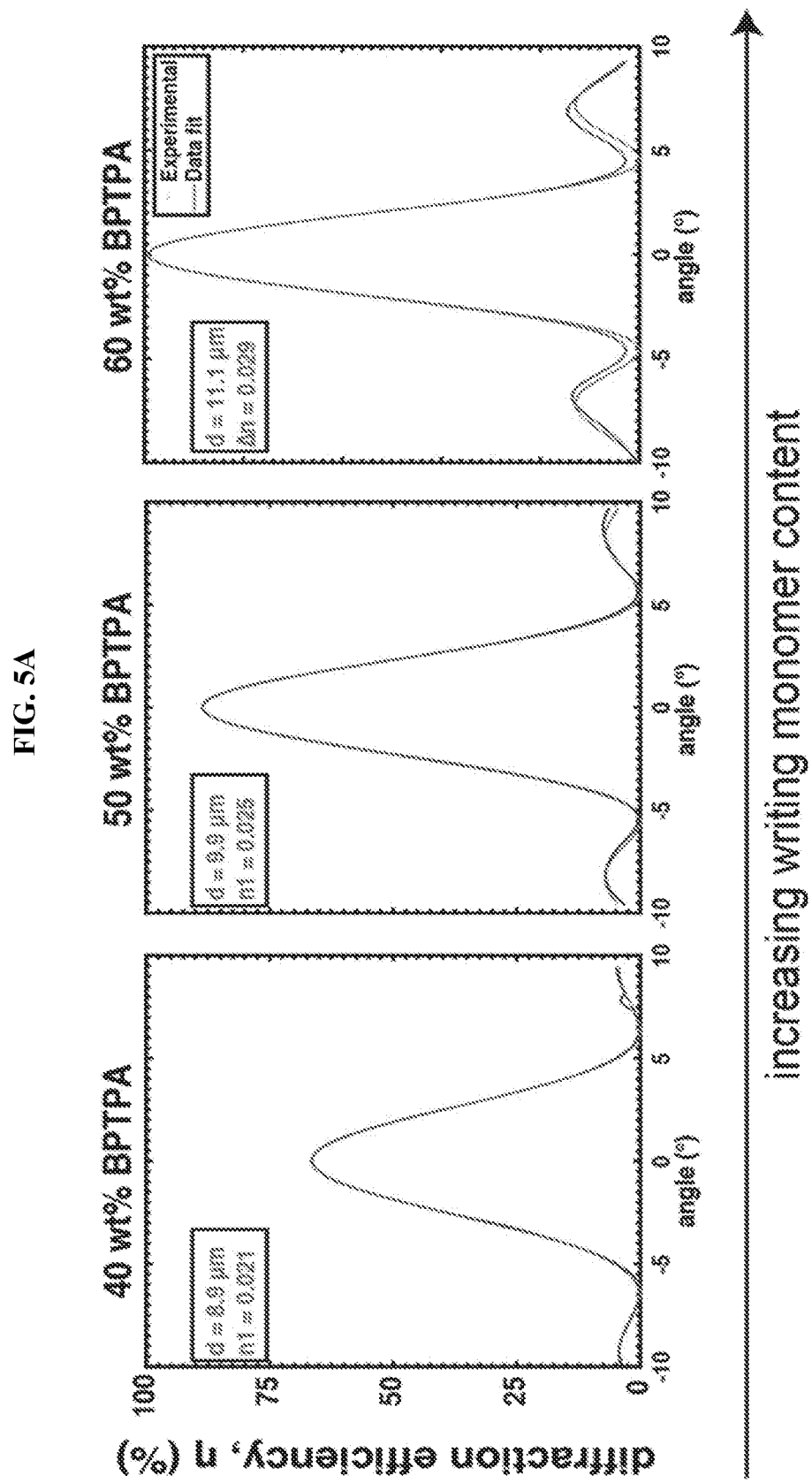
FIGS. 5A-5B are transmission holography and Δn (peak-to-mean) values recorded with a pitch spacing of 1 μm at a recording intensity of 16 mW/cm$^2$ with exposure times of 1s.
Figure 5B:
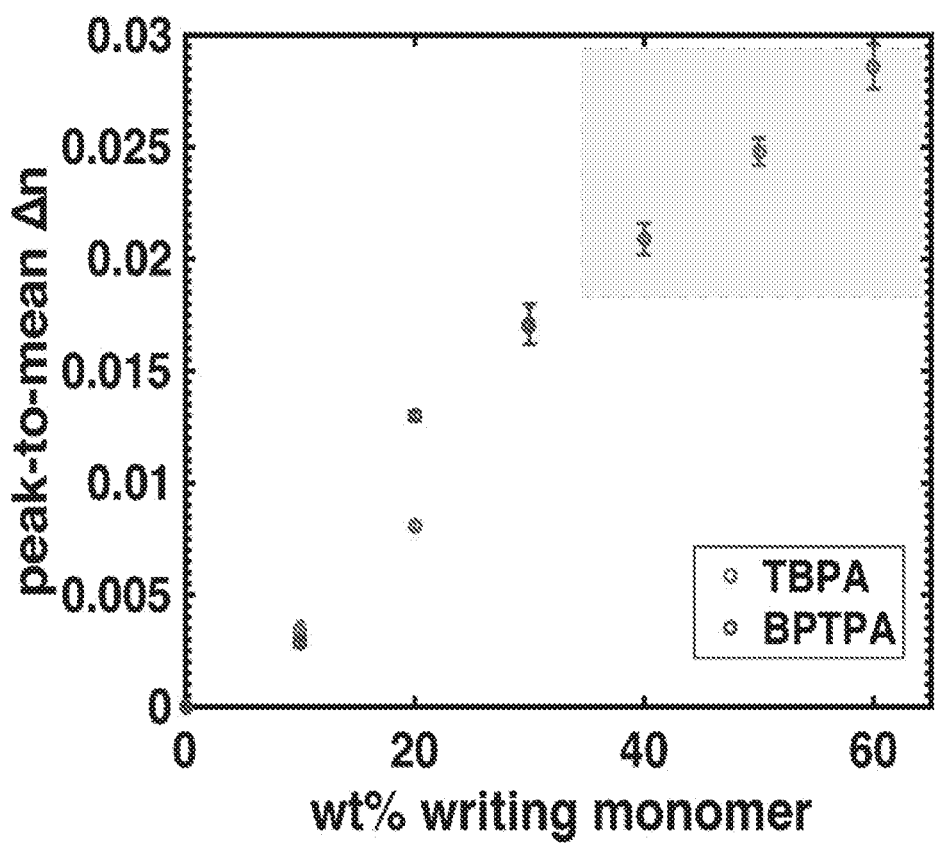

Based on the solubility studies together with the refractive index measurements, the data suggested that a significant overall Δn recording improvement could be gained from enhancements in both Δn/[M] as well as the amount of monomer that can be loaded. High diffraction efficiency transmission volume holograms (fringe spacing Λ≈1 μm) were recorded into the TBPA and BPTPA samples at varying monomer loadings in thin films (<15 μm) to intentionally avoid over-modulation. Representative angular scans with good fits to Kogelnik coupled wave theory are shown in FIG. 5A for samples containing 40, 50 and 60 wt % BPTPA with a peak-to-mean Δn of up to 0.029 demonstrated. FIG. 5B shows the overall maximum achievable Δn for both writing monomers at increasing wt % loading. By increasing the writing monomer loading, the observed Δn of a given material was increased without a noticeable penalty in transparency or scatter. An additional advantage of the increased solubility of BPTPA was the boost in material sensitivity due to a concomitant increase in the polymerization rate that arose from the higher monomer concentration.

High sensitivity materials are especially critical for holography due to laser source limitations in power and overall setup stability time. This feature also extends to alternative photoinitiating systems which initiate at longer visible wavelengths but are less efficient.

Example 6: Bulk Δn Vs. Holographic Δn Analysis

Figure 6:
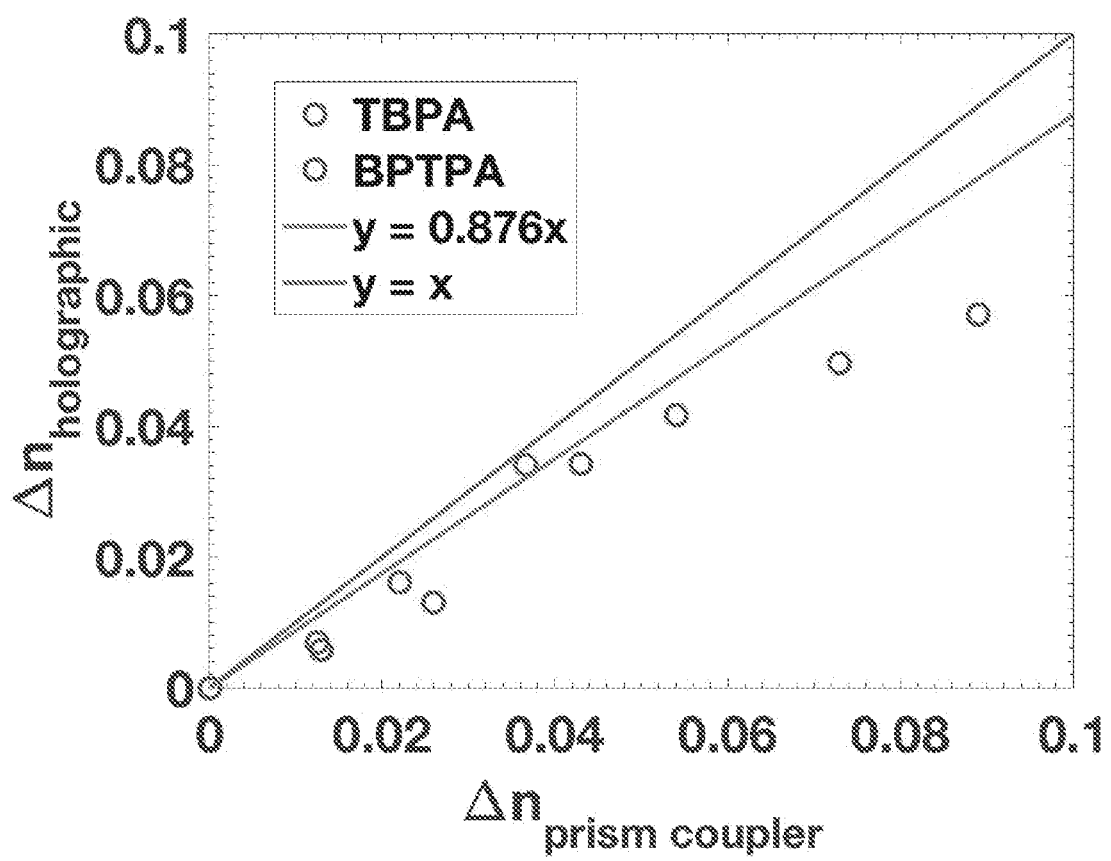
FIG. 6 is a graph showing an "effective" refractive index contrast plot—achievable Δn with a sinusoidal intensity exposure measured via holography vs. the achievable Δn in bulk measured via prism coupler for TBPA and BPTPA at varying writing monomer content. The upper line (y=x) specifies the ideal case for a perfect match between refractive index contrast in bulk and holographic materials. The lower line indicates the actual theoretical maximum Δn (88%) to be expected from the holographic Δn measured which only measures the first harmonic.
Figure 8:
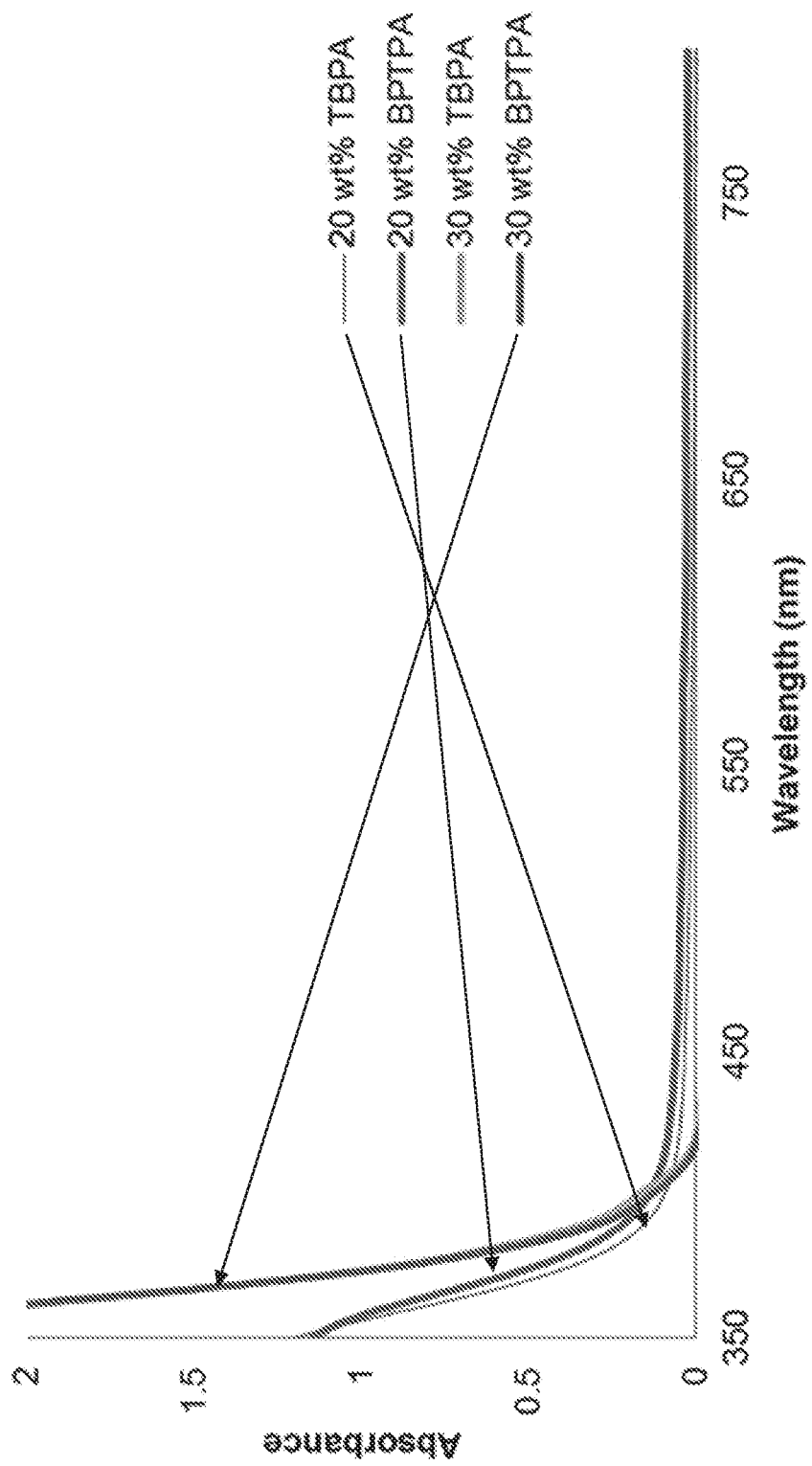
FIG. 8 is a graph showing the UV-vis absorption spectra of TBPA and BPTPA formulations before stage 2 polymerization.
Figure 9:
FIG. 9 is a photograph of a vial of a composition of the invention showing loss of transparency of precursor resins at higher TBPA loadings (50 wt %)

Achievable holographic Δn in two-stage materials from a sinusoidal exposure is a fraction of the maximum achievable index response from a uniform flood-cure. For a single holographic exposure (two-beam interference), it can be shown that the highest achievable Δn of the first harmonic is approximately 88% of a material's maximum refractive index response (see Example 8). In FIG. 6 the holographic Δn is plotted against the bulk Δn between stage 1 and 2 as measured using a prism coupler for both writing monomers. These results indicate that although BPTPA was able to achieve a higher holographic Δn through the increased solubility there is also a decrease in the "efficacy" of the increased index contrast at higher loadings.

Example 7: Refractive Index Gradient Demonstrations

Refractive index structures at low spatial frequencies were also demonstrated using direct laser write (DLW) of an arbitrary pattern and projection lithography using a Fresnel lens etched chrome mask. The DLW example (FIG. 7A) demonstrated distinct refractive index contrast between the photopolymer of BPTPA and the matrix whilst the Fresnel lens (FIG. 7B) example validated the ability to record a structure with a fine gradient in refractive index. As evidenced by the stitched bright field DIC microscope (Nikon N-STORM) images in FIGS. 7A-7B the material was able to record distinct sub-micron to tens of microns-sized features with excellent fidelity in both cases.

Example 8: Refractive Index Contrast Measurable by a Single Bragg Hologram

The transmission Bragg hologram used to characterize material refractive index contrast is an imperfect measurement as the material saturates due to consumption of monomer. Specifically, in certain instances, sinusoidal writing intensity consumes a significant fraction of the monomer species. As this first-order reaction proceeds, reduction of the monomer concentration proportionally reduces the propagation rate. The index of refraction thus saturates according to $$\frac{\delta n(x)}{\Delta n} = 1 - e^{-E(x)/E_c}, \quad \text{Eq. 1}$$

where $\delta n$ is the local index change, $\Delta n$ is the maximum index change that occurs upon full conversion, $E(x)$ is the local optical dose and $E_c$ is the dose that consumes a fraction $1/e$ of the initial monomer concentration.

Figure 10:
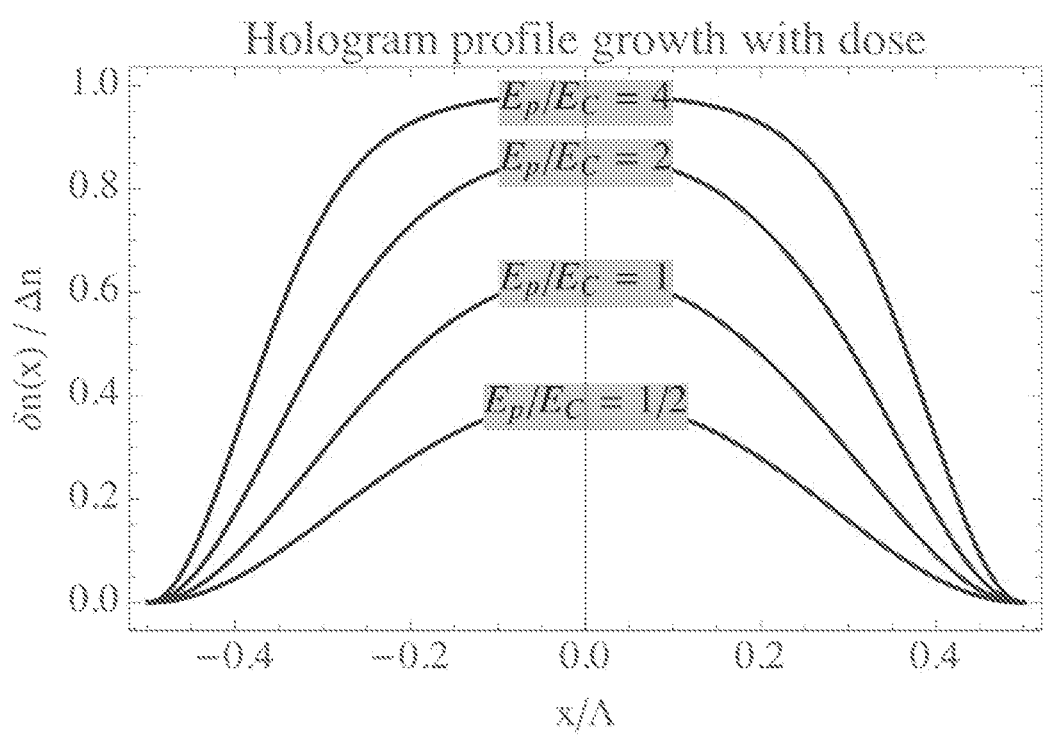
FIG. 10 is a graph showing a set of index profiles δn normalized to the maximum index change Δn over one period of the interferogram, Λ. The sinusoidal response saturated as the peak dose, $E_p$, became large in comparison to the critical exposure dose $E_C$.

For two-beam interference writing, the local optical dose $E(x)$ is given by $$E(x) = E_p \left[ 1 + \cos\left(2\pi - \frac{x}{\Lambda}\right)\right]/2, \quad \text{Eq. 2}$$

where $E_p$ is the peak dose and $\Lambda$ is the period of the writing sinusoid. As the peak dose $E_p$ becomes significant in comparison to the dose that consumes $1/e$ of the concentration, the response saturates, resulting in flattened peaks as shown in FIG. 10.

Diffraction off of such a phase structure will depend on the Fourier harmonics of the fundamental spatial frequency $1/\Lambda$. To obtain a quasi-closed form for the Fourier series $$\delta n(x) = \sum_{m=0}^{\infty} n_m \cos\left(2\pi m \frac{x}{\Lambda}\right),$$

Eq. 1 is expanded in a power series in x, substitute in Eq. 2 and gather the coefficients of the $m^{th}$ harmonic. The initial terms in this series for the first three harmonics are $$\frac{n_1}{\Delta n} = \frac{1}{2}\left(\frac{E_p}{E_C}\right) - \frac{1}{2}\left(\frac{E_p}{E_C}\right)^2 + \quad \text{Eq. 3}$$

$$\frac{5}{64}\left(\frac{E_p}{E_C}\right)^3 - \frac{7}{384}\left(\frac{E_p}{E_C}\right)^4 + \frac{7}{2048}\left(\frac{E_p}{E_C}\right)^5 + O\left[\left(\frac{E_p}{E_C}\right)^6\right],$$

$$\frac{n_2}{\Delta n} = 0\left(\frac{E_p}{E_C}\right) - \frac{1}{16}\left(\frac{E_p}{E_C}\right)^2 + \frac{1}{32}\left(\frac{E_p}{E_C}\right)^3 -$$

$$\frac{7}{768}\left(\frac{E_p}{E_C}\right)^4 + \frac{1}{512}\left(\frac{E_p}{E_C}\right)^5 + O\left[\left(\frac{E_p}{E_C}\right)^6\right],$$

$$\frac{n_3}{\Delta n} = 0\left(\frac{E_p}{E_C}\right) + 0\left(\frac{E_p}{E_C}\right)^2 + \frac{1}{192}\left(\frac{E_p}{E_C}\right)^3 -$$

$$\frac{1}{384}\left(\frac{E_p}{E_C}\right)^4 + \frac{3}{4096}\left(\frac{E_p}{E_C}\right)^5 + O\left[\left(\frac{E_p}{E_C}\right)^6\right].$$

Figure 11:
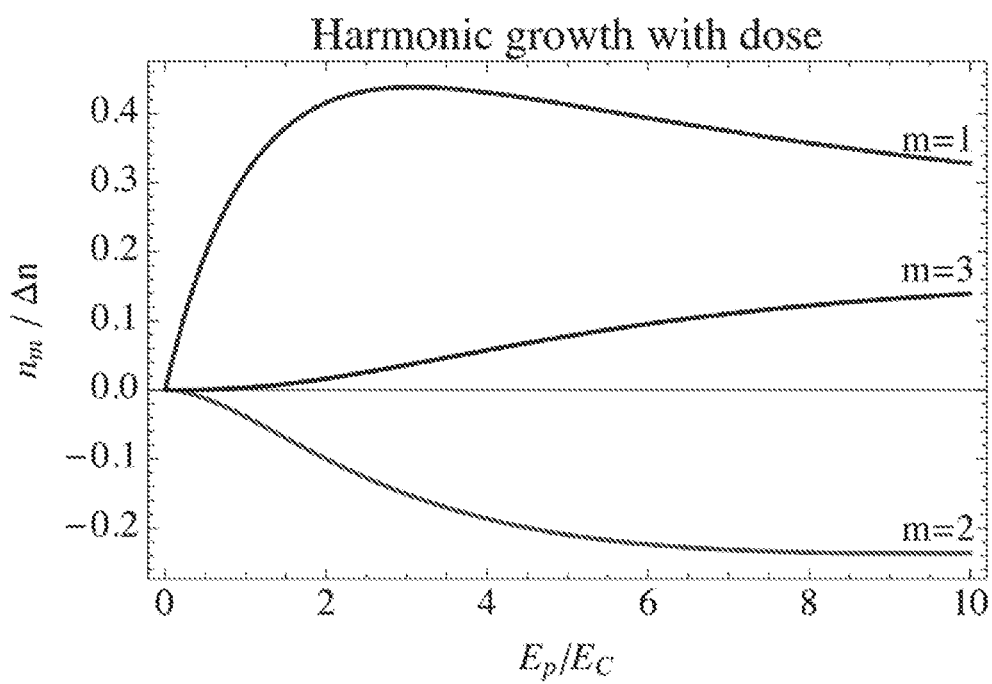
FIG. 11 is a graph of the first through third harmonic of the recorded index change relative to the maximum index change Δn as a function of the peak dose, $E_p$ relative to the critical exposure dose $E_C$. Note that $n_m$ is the peak to mean amplitude and thus is bounded by +½. The functions plotted are given in Eq. 3 using the first 100 terms of the series.
Figure 12:
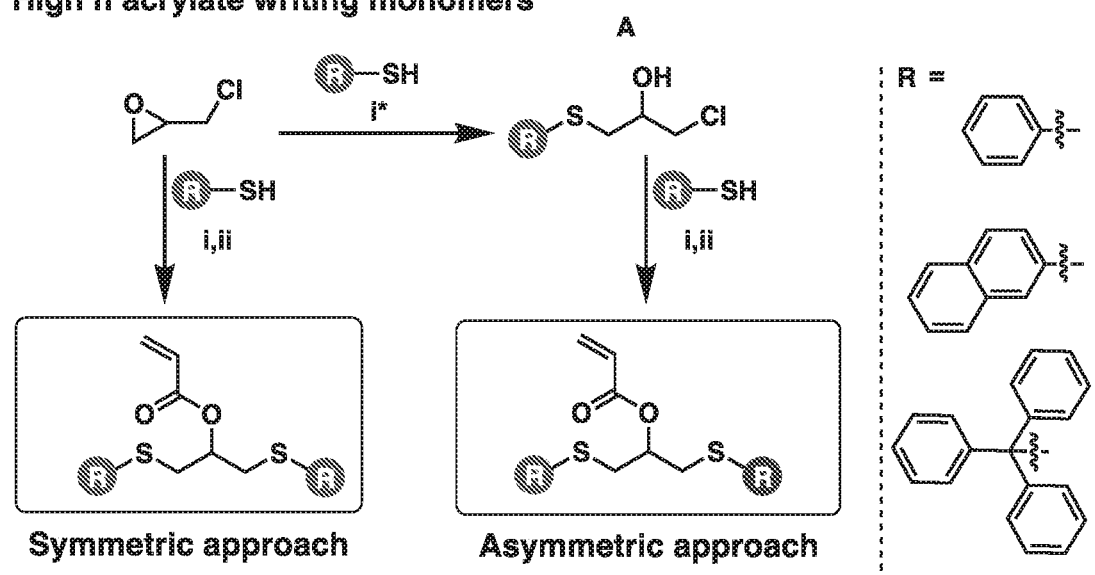
FIG. 12 is a scheme showing the synthetic routes for symmetric or asymmetric high refractive index acrylate writing monomers. The symmetric approach (one thiol) involves two steps: i) RSH, 1,8-Diazabicyclo(5.40)undec-7-ene (DBU), toluene, room temperature (RT), 16 h; ii) Acryloyl chloride, triethylamine (TEA), 4-(dimethylamino) pyridine (DMAP), dichloromethane (DCM), room temperature (RT), 16 h. The asymmetric approach (two thiols) involves three steps with the additional i* step being the thiol-epoxy ring-opening reaction to generate the chlorinated secondary alcohol intermediate A.

These reveal that, to lowest order, the $m^{th}$ harmonic grows as the peak dose to the $m^{th}$ power. These are plotted in FIG. 11. The maximum of the first harmonic is $n_1 \approx 0.438$ at a peak dose of $E_p \approx 3.09 E_C$, indicating that only 88% of the material maximum index response can be accessed with single-exposure two beam interference.

Example 9: Monomers of the Invention

Acrylate Writing Monomers

Figure 14:
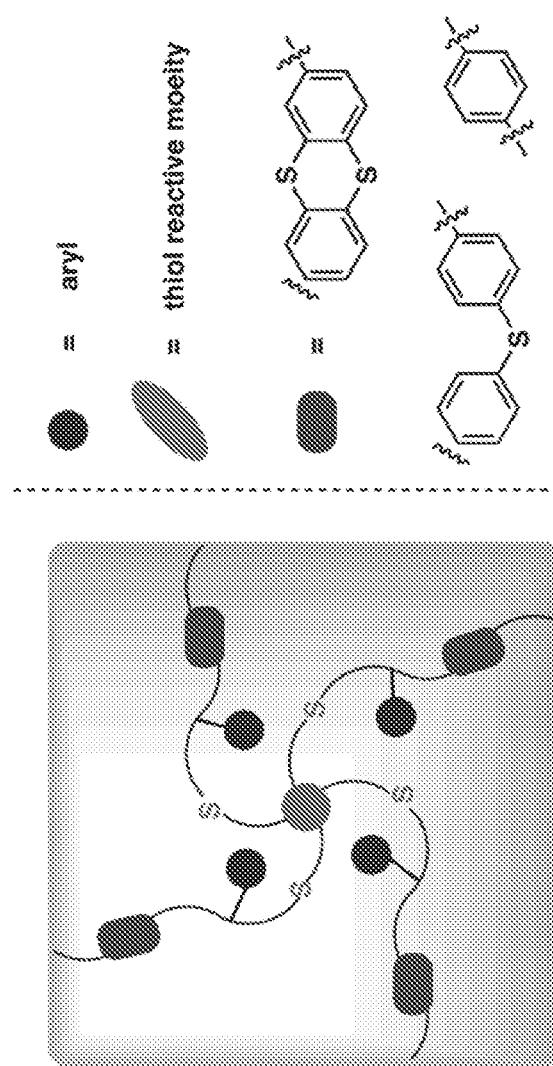
FIG. 14 is a scheme for high refractive index and crosslinked thiol-X networks with design tunability in the linker, core(s) or polymerizable functional group.
Figure 14:
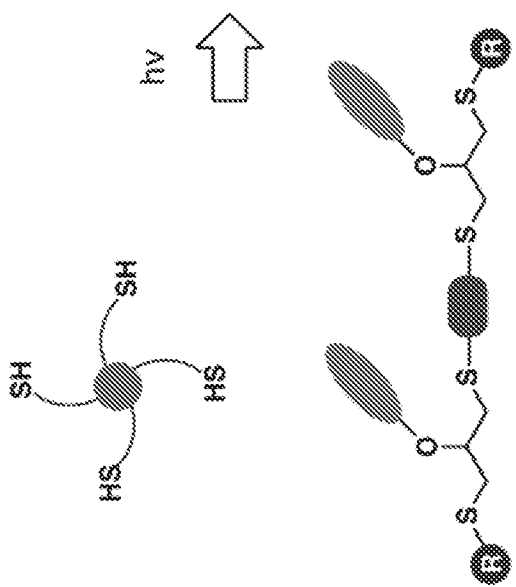

Symmetric or asymmetric acrylate writing monomers exhibiting high refractive index ($n_D$ values up to 1.66 for the monomers) have been synthesized using the approach outlined in FIG. 14. Either approach employs epichlorohydrin and a monofunctional high refractive index thiol (or thiols). In the symmetric case, using excess thiol (>2 equiv.) with base engenders the thiol-epoxy and thiol-halide reaction to yield the secondary alcohol intermediate. For the asymmetric case, one thiol ($R^1$—SH) can be used for only the thiol-epoxy reaction rendering the chloro intermediate A, that can then be subsequently reacted with another high refractive index thiol ($R^2$—SH) to generate the asymmetric secondary alcohol intermediate. From the secondary alcohol intermediates, standard acylation procedures are employed to produce the acrylate monomers. These monomers are liquid at room temperature with low viscosities and at least 50 wt % solubility exhibited in prepared two-stage formulations using a base urethane matrix. As discussed elsewhere herein, incorporating the symmetric thiophenol-based acrylate writing monomer, 1,3-bis-(phenylthio)-2-propyl acrylate (BPTPA), showed marked increases in two-stage formulation solubility and an achievable holographic (peak-to-mean) $\Delta n$ approaching 0.03 for a 1 μm fringe spacing in an otherwise unoptimized formulation. Given that the $n_D$ of BPTPA is comparatively low at 1.6028 amongst the set of synthesized writing monomers, realizing $\Delta n$ that exceed 0.03 is conceivable.

TABLE 2 characterization of BPTPA: 1,3-bis(phenylthio)-2-propyl acrylate, BMTPTPA: 1,3-bis((methylthio)phenylthio)-2-propyl acrylate, BNTPA: 1,3-bis(naphthylthio)-2-propylacrylate

| MONOMERS | $n_D$ | $n_F$ | $n_C$ | V |
|---|---|---|---|---|
| BPTPA | 1.602792 | 1.618768 | 1.596657 | 27.3 |
| BMTPTPA | 1.640769 | 1.661502 | 1.640769 | 30.9 |
| BNTPA | 1.661435 | 1.685874 | 1.652366 | 19.7 |

TABLE 3 characterization of BPTPA polymer p(BPTA) and BMTPTPA polymer p(BMTPTPA)

| POLYMERS | $n_D$ | $n_F$ | $n_C$ | V |
|---|---|---|---|---|
| p(BPTPA) | 1.633974 | 1.650459 | 1.627643 | 27.79 |
| p(BMPTPA) | 1.670452 | 1.691466 | 1.662627 | 23.25 |

Figure 13:
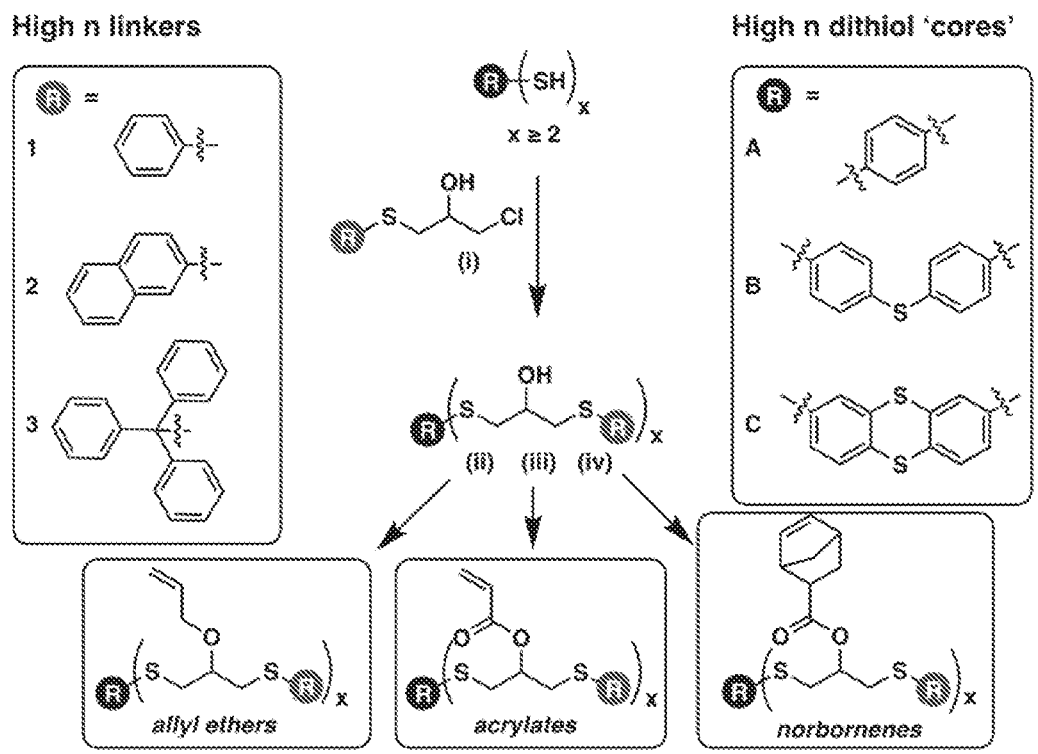
FIG. 13 is a scheme showing the synthetic strategy towards designed thiol-X writing monomers. Given a high refractive index linker with a multifunctional thiol (i) 1,8-Diazabicyclo(5.40)undec-7-ene (DBU), toluene, RT, 16 h; The allyl ethers were made using ii) allyl bromide, sodium hydride (NaH), tetrahydrofuran (THF), 0° C.→room temperature (RT), 16 h; The acrylates were made using iii) Acryloyl chloride, triethylamine (TEA), 4-(dimethylamino) pyridine (DMAP), dichloromethane (DCM), room temperature (RT), 16; The norbornenes were made using iv) norbomene carboxylic acid, N,N'-Dicyclohexylcarbodiimide (DCC), dichloromethane (DCM), room temperature (RT), 16 h.
Figure 13:
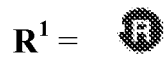
Figure 13:
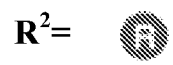

Designed thiol and 'ene' writing monomers extend refractive index (thioether linkage) whilst utilizing the exceptional advantages of the step-growth thiol-ene 'click' reaction such as negligible oxygen sensitivity and reduced shrinkage. Toward this goal, a general synthetic strategy was devised to generate a library of writing monomers with high structural tunability to control material properties such as refractive index, dispersion, viscosity, glass transition temperature, etc.

as shown in FIG. 13. This approach involves high refractive index linkers (intermediate in the asymmetric acrylate procedure) with multifunctional high refractive index thiol 'cores' to yield multifunctional secondary alcohols that can be functionalized to achieve various reactive groups such as allyl ethers, (meth)acrylates, alkynes, norbornenes and even thiols.

Using high n linker 1 and dithiol cores A, B and C, systematically varying sets of diallyl ether writing monomers were synthesized displaying $n_D$ values up to 1.66. These synthesized compounds were liquids soluble in neat thiol-ene resins unlike their underlying thiol 'cores'. Photopolymerization of a neat thiol-ene resin using 1,3,5-benzene trimethanethiol yielded $n_D$ values exceeding 1.7 using the 1C diallyl ether. Higher refractive index and crosslink density networks were readily achievable using an appropriate tetrafunctional thiol instead such as 1,2,4,5-benzene tetrathiol as illustrated in FIG. 14.

TABLE 4 characterization of 1,4-benzene dithiol-based diallyl ether (BDTDAE), 4,4'-thiobisbenzenethiol-based diallyl ether (TBTDAE), 2,7-thianthrene dithiol-based diallyl ether TDTDAE:

| MONOMERS | $n_D$ | $n_F$ | $n_C$ | V |
|---|---|---|---|---|
| BDTDAE | 1.61682 | 1.63416 | 1.61027 | 25.8 |
| TBTDAE | 1.644039 | 1.664747 | 1.636233 | 22.6 |
| TDTDAE | 1.660075 | 1.680077 | 1.652236 | 23.7 |

Thiol-Capped Oligomers

Figure 15:
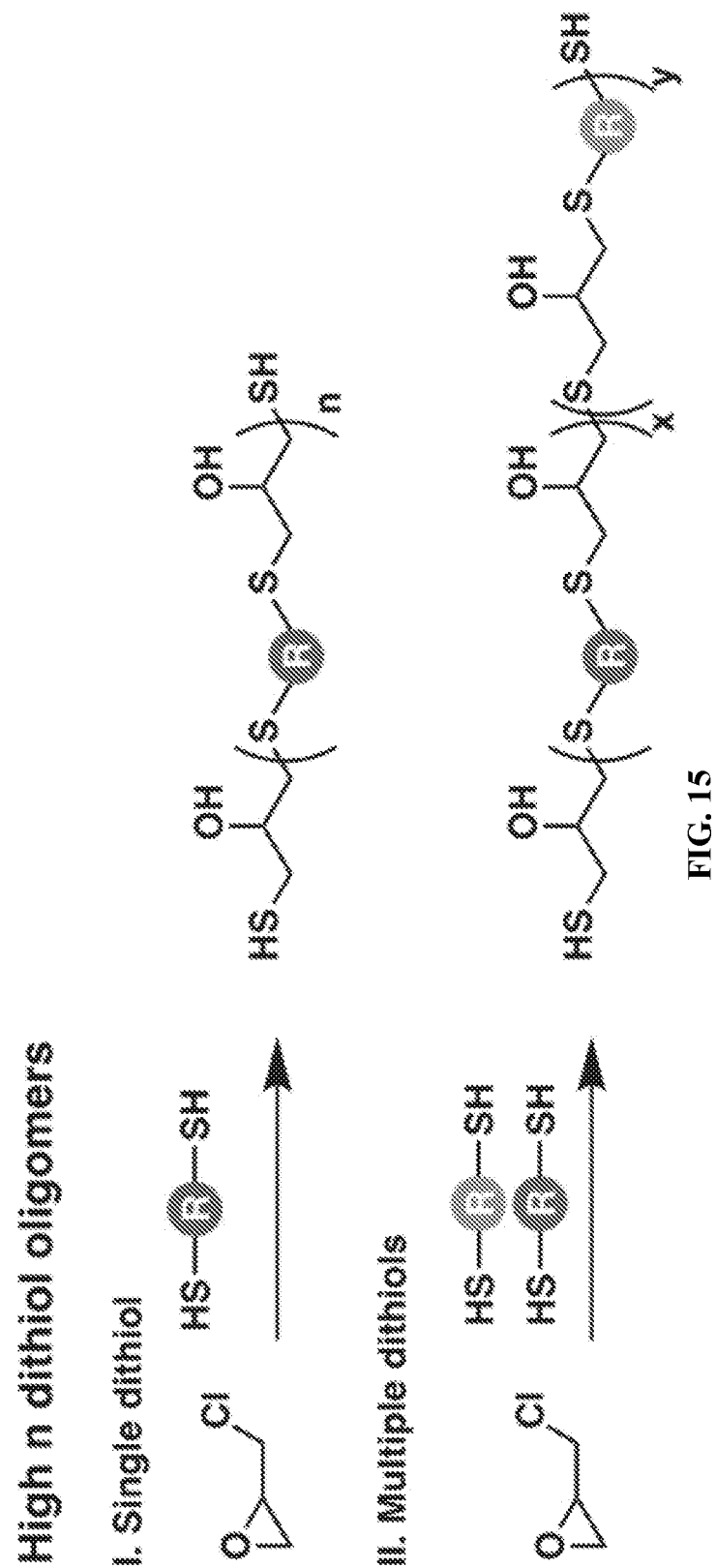
FIG. 15 is a scheme for producing high refractive index dithiol oligomers capable of thiol-X polymerizations as well as further post-functionalization of the pendant secondary alcohol groups present at every repeat unit. Excess of dithiol(s) is reacted with epichlorohydrin under basic conditions via a combined thiol-epoxy and thiol-halide reaction. The judicious choice of multiple dithiols can further enable interesting material properties.

High refractive index thiol-capped oligomers extend the accessible range of material properties in thiol-ene formulations. Such dithiol oligomers can be prepared under basic conditions via the combined thiol-epoxy and thiol-halide reaction of epichlorohydrin with a high refractive index dithiol (or dithiols) used in slight excess to ensure thiol end-groups. The molecular weights of the oligomers can be precisely controlled via off-stoichiometry ratios while the pendant secondary alcohol groups present at every repeat unit are amenable to further post-functionalization. Furthermore, use of multiple dithiols can achieve unique mechanical and optical properties similar to block copolymers with hard and soft segments based on the R group chosen for the dithiols (alkyl or aromatic) as illustrated in FIG. 15.

Enumerated Embodiments

The following exemplary embodiments are provided, the numbering of which is not to be construed as designating levels of importance:

Embodiment 1 provides a monomer of formula (I):

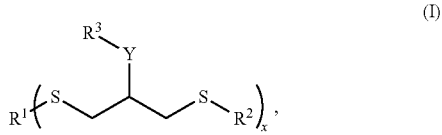

wherein, each instance of $R^1$ and $R^2$ is independently selected from the group consisting of optionally substituted $C_6$-$C_{15}$ aryl, optionally substituted $C_5$-$C_{18}$ heteroaryl, and $C_1$-$C_3$ alkyl optionally substituted with 1-6 independently selected $C_6$-$C_{10}$ aryl groups; $R^3$ is selected from the group consisting of optionally substituted $C_2$-$C_{15}$ alkenyl, optionally substituted $C_2$-$C_{15}$ heteroalkenyl, optionally substituted $C_2$-$C_{15}$ alkynyl, optionally substituted $C_2$-$C_{15}$ heteroalkynyl, optionally substituted —C(=O)—$C_2$-$C_{15}$ alkenyl, optionally substituted —C(=O)—$C_2$-$C_{15}$ alkynyl, optionally substituted —C(=O)—$C_3$-$C_{10}$ cycloalkenyl, optionally substituted $C_3$-$C_{10}$ cycloalkenyl, and optionally substituted $C_3$-$C_{10}$ heterocycloalkenyl; and x is an integer ranging from 1 to 4.

Embodiment 2 provides the monomer of embodiment 1, wherein $R^3$ is selected from the group consisting of

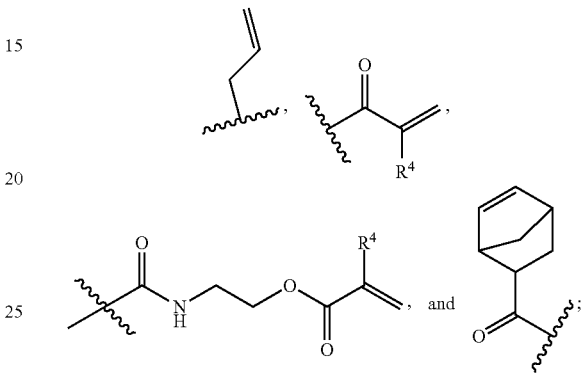

wherein $R^4$ is selected from the group consisting of H and —CH$_3$.

Embodiment 3 provides the monomer of any one of embodiments 1-2, wherein $R^1$ and $R^2$ are each independently selected from the group consisting of

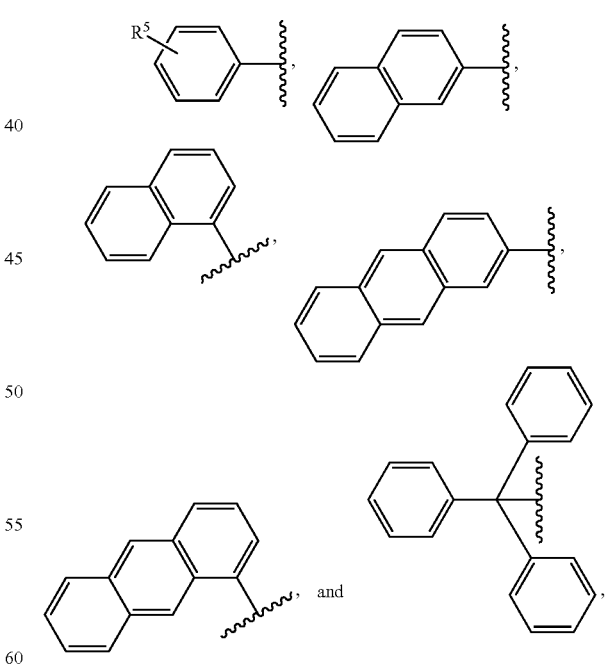

wherein $R^5$ is selected from the group consisting of H, optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ hetero alkenyl, optionally substituted $C_2$-$C_6$ alkynyl, optionally substituted $C_2$-$C_6$ heteroalkynyl.

Embodiment 4 provides the monomer of any one of embodiments 1-3, wherein if x is 1 and $R^3$ is

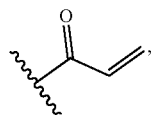 [SMILES: *C(=O)C=C]

then one of $R^1$ or $R^2$ is not phenyl.

Embodiment 5 provides the monomer of any one of embodiments 1-4, wherein $R^1$ selected from the group consisting of

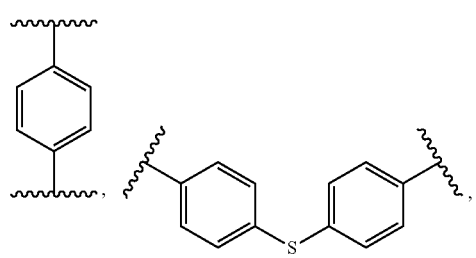 [SMILES: *c1ccc(*)cc1 ; *c1ccc(Sc2ccc(*)cc2)cc1]

and

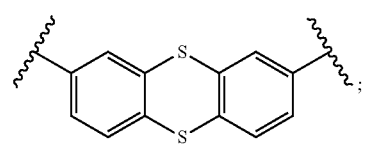 [SMILES: *c1ccc2c(c1)Sc1cc(*)ccc1S2]

each instance of $R^2$ is independently selected from the group consisting of

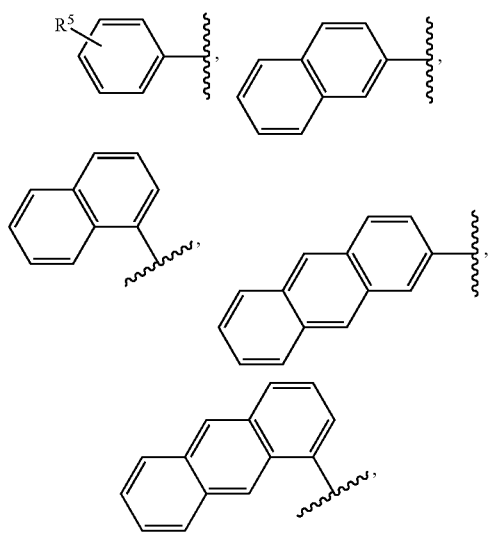

and

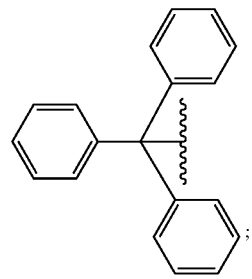 [SMILES: *C(c1ccccc1)(c1ccccc1)c1ccccc1]

$R^5$ is as described in claim 3; and x is 2.

Embodiment 6 provides the monomer of any one of embodiments 1-5 wherein the monomer is selected from the group consisting of (Ia)

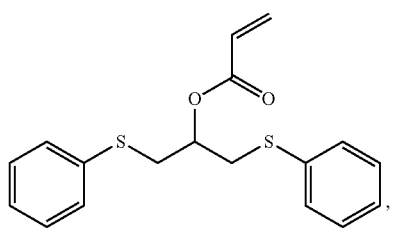

(Ib)

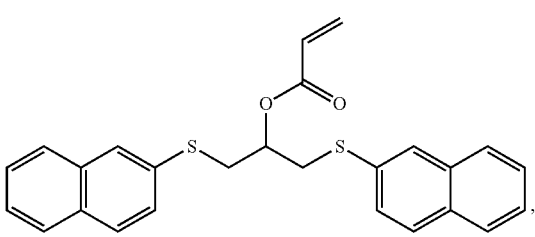

(Ic)

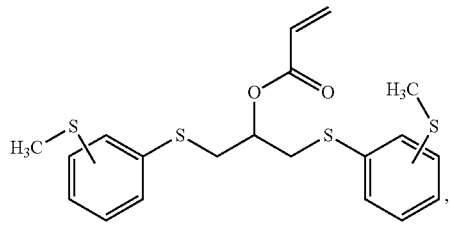

(Id)

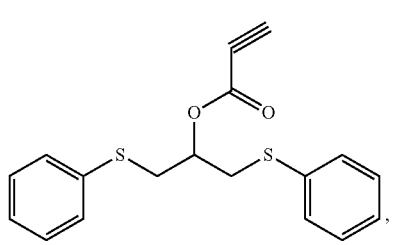

and

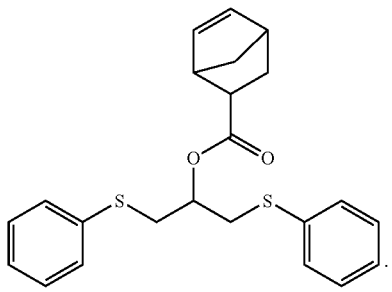

(Ie)

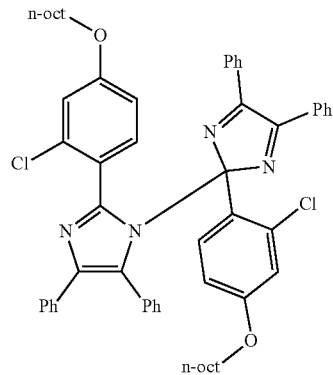

and

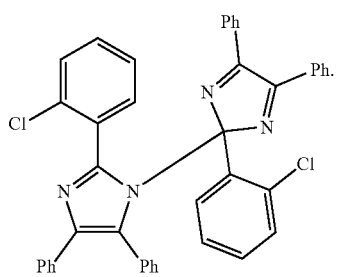 [SMILES: Clc1ccccc1-c1nc(-c2ccccc2)c(-c2ccccc2)n1C1(c2ccccc2Cl)N=C(c2ccccc2)C(c2ccccc2)=N1]

Embodiment 7 provides the monomer of any one of embodiments 1-6, wherein the monomer is selected from the group consisting of 1,3-bis(phenylthio)propan-2-yl acrylate, 1,3-bis(naphthalen-2-ylthio)propan-2-yl acrylate, (2-(prop-2-yn-1-yloxy)propane-1,3-diyl)bis(phenylsulfane), and 1,3-bis(phenylthio)propan-2-yl bicyclo[2.2.1]hept-5-ene-2-carboxylate.

Embodiment 8 provides the monomer of any one of embodiments 1-7, wherein the monomer has a refractive index of greater than about 1.6.

Embodiment 9 provides the monomer of any one of embodiments 1-8, wherein the monomer is photopolymerizable.

Embodiment 10 provides a polymer comprising the monomer of any one of embodiments 1-91, wherein the polymer is a holographic photopolymer.

Embodiment 11 provides the polymer of embodiment 10, wherein the polymer has refractive index of about 1.6 to about 1.7.

Embodiment 12 provides a composition comprising, the monomer of any one of embodiments 1-9, a matrix having a refractive index of less than about 1.5, and at least one photoinitiator.

Embodiment 13 provides the composition of embodiment 12, wherein the matrix comprises an urethane.

Embodiment 14 provides the composition of any one of embodiments 12-13, wherein the at least one photoinitiator is selected from the group consisting of acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4'-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide, Ethyl (2,4,6-trimethylbenzoyl) phenyl phosphinate, lithium phenyl-2,4,6-trimethylbenzoylphosphinate, Embodiment 15 provides the composition of any one of embodiments 12-14, wherein the composition is thermally cured at the temperature of about 50° C. to about 90° C.

Embodiment 16 provides the composition of any one of embodiments 12-15, wherein the composition is further photopolymerized using UV radiation.

Embodiment 17 provides the composition of any one of embodiments 12-16, wherein the difference in the refractive index (Δn) of the matrix and the polymer is greater than about 0.02.

Embodiment 18 provides the composition of any one of embodiments 12-17, wherein the composition is useful for making holograms.

Embodiment 19 provides a thiol-capped oligomer of formula (II):

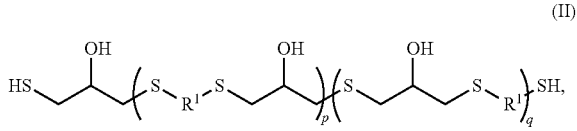

(II)

wherein, $R^1$ is selected from the group consisting of optionally substituted $C_6$-$C_{18}$ aryl, optionally substituted $C_5$-$C_{15}$ heteroaryl, and $C_1$-$C_3$ alkyl optionally substituted with 1-6 independently selected $C_6$-$C_{10}$ aryl groups; p is any integer ranging from 2 to 200; and q is an integer ranging from 0 to 200.

Embodiment 20 provides a method of preparing a holographic polymer, the method comprising: polymerizing the composition of any of embodiments 12-18 to provide a holographic polymer.

Embodiment 21 provides a method of embodiment 20, wherein the polymerizing comprises thermally curing the composition at a temperature of about 50° C. to about 90° C.

Embodiment 22 provides a method of any one of embodiments 20-21, wherein the polymerizing further comprises photopolymerizing the composition using UV radiation.

Embodiment 23 provides a method of any one of embodiments 20-22, wherein the at least one photoinitiator is selected from the group consisting of acetophenone, benzophenone, 2-phenylacetophenone, 2,2-dimethoxy-2-phenylacetophenone, Bis(2,4,6-trimethylbenzoyl)-phenylphosphineoxide, 2-Hydroxy-4'-(2-hydroxyethoxy)-2-methylpropiophenone, 2-methyl-(4-methylthienyl)-2-morpholinyl-1-propan-1-one, Diphenyl(2,4,6-trimethylbenzoyl)phosphine oxide, Ethyl (2,4,6-trimethylbenzoyl) phenyl phosphinate, lithium phenyl-2,4,6-trimethylbenzoylphosphinate,

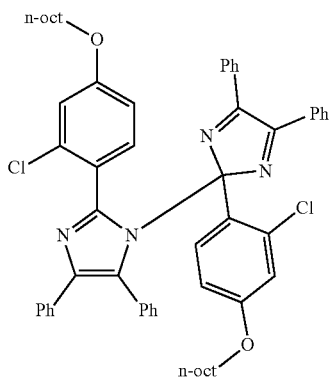

and

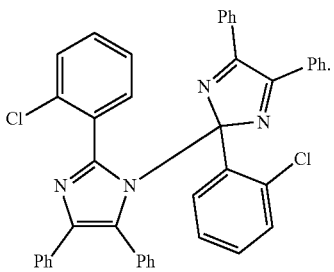 [SMILES: Clc1ccccc1-c1nc(-c2ccccc2)c(-c2ccccc2)n1C1(c2ccccc2Cl)N=C(c2ccccc2)C(c2ccccc2)=N1]

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A monomer of formula (I):

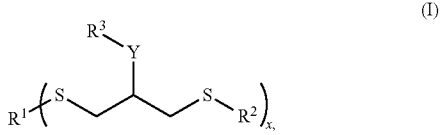

wherein:

each instance of Y is independently O, S, or NH;

each instance of $R^2$ is independently selected from the group consisting of:

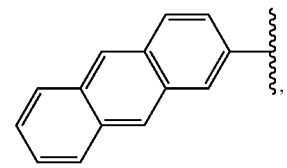

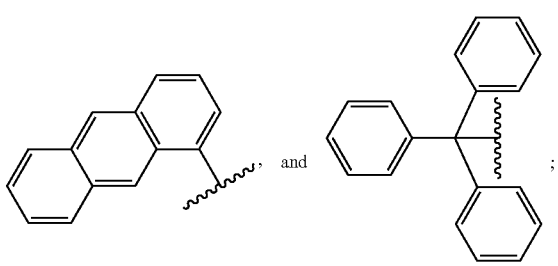

x is 1 or 2, wherein:

x is 1 and $R^1$ is independently selected from the group consisting of:

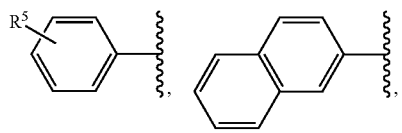

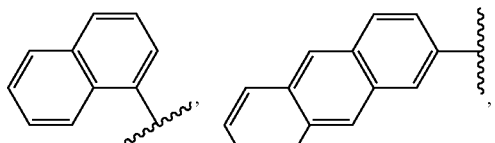

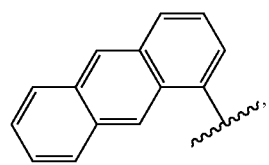

33

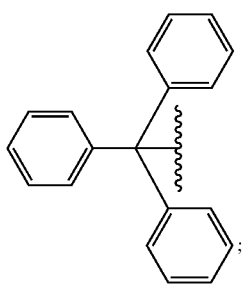 [SMILES: *C(c1ccccc1)(c1ccccc1)c1ccccc1]

or x is 2 and R¹ is independently selected from the group consisting of:

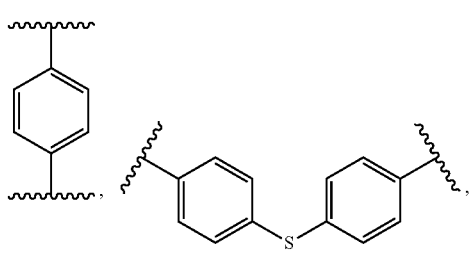

and

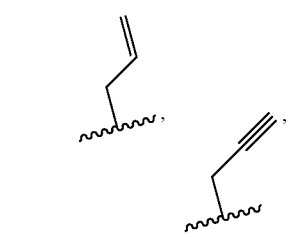

R³ is selected from the group consisting of:

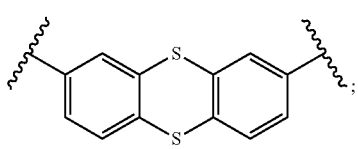 [SMILES: *c1ccc2c(c1)Sc1cc(*)ccc1S2]

34 and

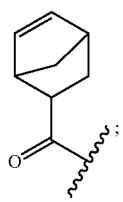 [SMILES: *C(=O)C1CC2C=CC1C2]

$R^4$ is selected from the group consisting of H and —CH$_3$;

$R^5$ is selected from the group consisting of H, optionally substituted C$_1$-C$_6$ alkyl, optionally substituted C$_1$-C$_6$ heteroalkyl, optionally substituted C$_2$-C$_6$ alkenyl, optionally substituted C$_2$-C$_6$ heteroalkenyl, optionally substituted C$_2$-C$_6$ alkynyl, and optionally substituted C$_2$-C$_6$ heteroalkynyl.

2. The monomer of claim 1, wherein x is 2 and R¹ is selected from the group consisting of:

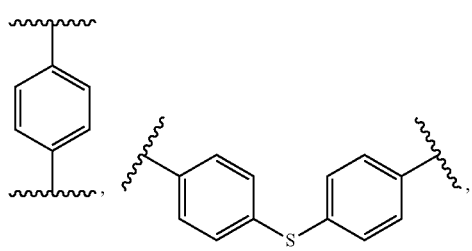

and

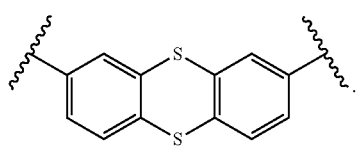 [SMILES: *c1ccc2c(c1)Sc1cc(*)ccc1S2]

3. The monomer of claim 1, which has a refractive index of greater than about 1.6.

4. The monomer of claim 1, which is photopolymerizable.

5. The compound of claim 1, wherein R³ is

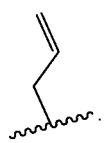

6. The compound of claim 1, wherein R³ is

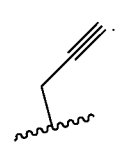

7. The compound of claim 1, wherein R³ is

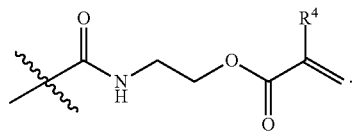

8. The compound of claim 1, wherein R³ is

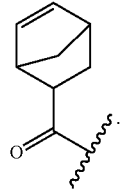 [SMILES: *C(=O)C1CC2C=CC1C2]

9. A polymer comprising the monomer of claim 1, wherein the polymer is a holographic photopolymer.

10. The polymer of claim 9, which has a refractive index of about 1.6 to about 1.7.

11. A composition comprising the monomer of claim 1; a matrix having a refractive index of less than about 1.5; and at least one photoinitiator.

12. The composition of claim 11, wherein the matrix comprises an urethane.

13. The composition of claim 11, wherein the at least one photoinitiator is selected from the group consisting of acetophenone, benzophenone, 2-phenylacetophenone, 2,2-dimethoxy-2-phenylacetophenone, bis(2,4,6-trimethylbenzoyl)-phenylphosphineoxide, 2-hydroxy-4'-(2-hydroxyethoxy)-2-methylpropiophenone, 2-methyl-(4-methylthienyl)-2-morpholinyl-1-propan-1-one, diphenyl(2,4,6-trimethylbenzoyl)phosphine oxide, ethyl (2,4,6-trimethylbenzoyl) phenyl phosphinate, lithium phenyl-2,4,6-trimethylbenzoylphosphinate,

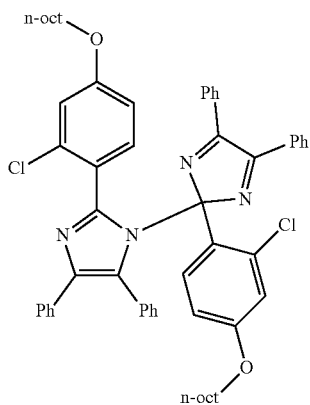

and

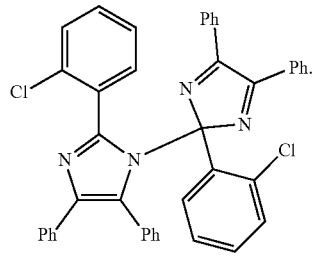

14. The composition of claim 11, which is thermally cured at a temperature of about 50° C. to about 90° C.

15. The composition of claim 14, which is further photopolymerized using UV radiation.

16. The composition of claim 11, wherein the difference in the refractive index (Δn) of the matrix and the polymer is greater than about 0.02.

17. A method of preparing a holographic polymer, the method comprising polymerizing the composition of claim 11 to provide a holographic polymer.

18. The method of claim 17, wherein the polymerizing comprises thermally curing the composition at a temperature of about 50° C. to about 90° C.

19. The method of claim 18, wherein the polymerizing further comprises photopolymerizing the composition using UV radiation.

20. The method of claim 19, wherein the at least one photoinitiator is selected from the group consisting of acetophenone, benzophenone, 2-phenylacetophenone, 2,2-dimethoxy-2-phenylacetophenone, bis(2,4,6-trimethylbenzoyl)-phenylphosphineoxide, 2-hydroxy-4'-(2-hydroxyethoxy)-2-methylpropiophenone, 2-methyl-(4-methylthienyl)-2-morpholinyl-1-propan-1-one, diphenyl(2,4,6-trimethylbenzoyl)phosphine oxide, ethyl (2,4,6-trimethylbenzoyl) phenyl phosphinate, lithium phenyl-2,4,6-trimethylbenzoylphosphinate,

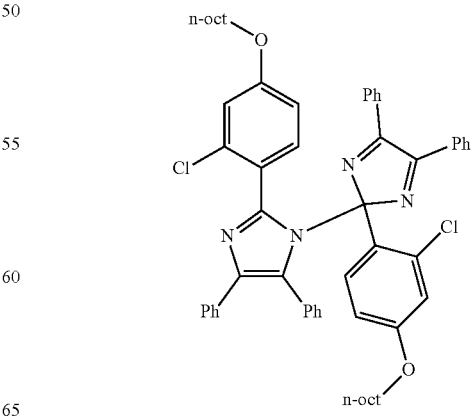

and
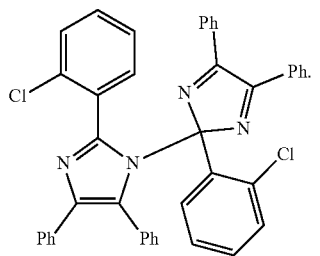 [SMILES: Clc1ccccc1-c1nc(-c2ccccc2)c(-c2ccccc2)n1C1(c2ccccc2Cl)N=C(c2ccccc2)C(c2ccccc2)=N1]
* * * * *